(12) United States Patent
Zamani et al.

(10) Patent No.: US 9,149,306 B2
(45) Date of Patent: Oct. 6, 2015

(54) SPINOUS PROCESS DEVICE

(75) Inventors: Shahram Shaun Zamani, San Diego, CA (US); Nicholas M. Cordaro, Vista, CA (US); Colin Matthew Smith, Dana Point, CA (US)

(73) Assignee: SeaSpine, Inc., Vista, CA (US)

( * ) Notice: Subject to any disclaimer, the term of this patent is extended or adjusted under 35 U.S.C. 154(b) by 124 days.

(21) Appl. No.: 13/530,049

(22) Filed: Jun. 21, 2012

(65) Prior Publication Data

US 2013/0012996 A1 Jan. 10, 2013

Related U.S. Application Data

(60) Provisional application No. 61/499,633, filed on Jun. 21, 2011.

(51) Int. Cl.
*A61B 17/70* (2006.01)
(52) U.S. Cl.
CPC .................................. *A61B 17/7068* (2013.01)
(58) Field of Classification Search
CPC .................................................... A61B 17/7068
USPC .......................... 606/246–249, 86 A, 99, 914
See application file for complete search history.

(56) References Cited

U.S. PATENT DOCUMENTS

| 5,102,412 | A | 4/1992 | Rogozinski |
| 5,454,812 | A | 10/1995 | Lin |
| 5,496,318 | A | 3/1996 | Howland et al. |
| 5,810,815 | A | 9/1998 | Morales |
| 5,836,948 | A | 11/1998 | Zucherman et al. |
| 6,048,342 | A | 4/2000 | Zucherman et al. |
| 6,068,630 | A | 5/2000 | Zucherman et al. |
| 6,074,390 | A | 6/2000 | Zucherman et al. |
| 6,090,112 | A | 7/2000 | Zucherman et al. |
| 6,149,652 | A | 11/2000 | Zucherman et al. |
| 6,152,926 | A | 11/2000 | Zucherman et al. |
| 6,156,038 | A | 12/2000 | Zucherman et al. |
| 6,183,471 | B1 | 2/2001 | Zucherman et al. |
| 6,190,387 | B1 | 2/2001 | Zucherman et al. |
| 6,235,030 | B1 | 5/2001 | Zucherman et al. |
| 6,238,397 | B1 | 5/2001 | Zucherman et al. |
| 6,280,444 | B1 | 8/2001 | Zucherman et al. |
| 6,332,882 | B1 | 12/2001 | Zucherman et al. |
| 6,332,883 | B1 | 12/2001 | Zucherman et al. |
| 6,364,883 | B1 | 4/2002 | Santilli |
| 6,379,355 | B1 | 4/2002 | Zucherman et al. |
| 6,419,676 | B1 | 7/2002 | Zucherman et al. |
| 6,419,677 | B2 | 7/2002 | Zucherman et al. |
| 6,451,019 | B1 | 9/2002 | Zucherman et al. |
| 6,451,020 | B1 | 9/2002 | Zucherman et al. |

(Continued)

*Primary Examiner* — Jan Christopher Merene
(74) *Attorney, Agent, or Firm* — McDermott Will & Emery LLP

(57) ABSTRACT

A device for immobilizing adjacent spinous processes can comprise a first element, a second element, and a spacer element. The first element can have a side configured to grip first sides of the adjacent spinous processes and a first separation bar that extends between the adjacent spinous processes when the first element and the spinous processes are engaged. The spacer element can have an adjustment bar and a second separation bar. The second element can have a side configured to grip second sides of the adjacent spinous processes and a clamping feature configured to selectably lock the first separation bar and the adjustment bar in place. The second separation bar can extend between the adjacent spinous processes when the second element and the adjacent spinous processes are engaged.

29 Claims, 21 Drawing Sheets

(56) References Cited

U.S. PATENT DOCUMENTS

| | | |
|---|---|---|
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,582,433 B2 | 6/2003 | Yun |
| 6,652,527 B2 | 11/2003 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,796,983 B1 | 9/2004 | Zucherman et al. |
| 6,902,566 B2 | 6/2005 | Zucherman et al. |
| 7,029,472 B1 | 4/2006 | Fortin |
| 7,029,473 B2 | 4/2006 | Zucherman et al. |
| 7,087,083 B2 | 8/2006 | Pasquet et al. |
| 7,101,375 B2 | 9/2006 | Zucherman et al. |
| 7,189,234 B2 | 3/2007 | Zucherman et al. |
| 7,201,751 B2 | 4/2007 | Zucherman et al. |
| 7,255,714 B2 | 8/2007 | Malek |
| 7,306,628 B2 | 12/2007 | Zucherman et al. |
| 7,318,825 B2 | 1/2008 | Butler et al. |
| 7,335,203 B2 | 2/2008 | Winslow et al. |
| 7,402,176 B2 | 7/2008 | Malek |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,510,567 B2 | 3/2009 | Zucherman et al. |
| 7,520,887 B2 | 4/2009 | Maxy et al. |
| 7,520,888 B2 | 4/2009 | Trieu |
| 7,524,324 B2 | 4/2009 | Winslow et al. |
| 7,549,999 B2 | 6/2009 | Zucherman et al. |
| 7,585,313 B2 | 9/2009 | Kwak et al. |
| 7,585,316 B2 | 9/2009 | Trieu |
| 7,588,591 B2 * | 9/2009 | Hartmann et al. ............ 606/249 |
| 7,588,592 B2 | 9/2009 | Winslow et al. |
| 7,591,851 B2 | 9/2009 | Winslow et al. |
| 7,601,170 B2 | 10/2009 | Winslow et al. |
| 7,611,526 B2 | 11/2009 | Carl et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,635,380 B2 | 12/2009 | Zucherman et al. |
| 7,662,187 B2 | 2/2010 | Zucherman et al. |
| 7,666,209 B2 | 2/2010 | Zucherman et al. |
| 7,682,376 B2 | 3/2010 | Trieu |
| 7,691,130 B2 | 4/2010 | Bruneau et al. |
| 7,695,513 B2 | 4/2010 | Zucherman et al. |
| 7,727,233 B2 | 6/2010 | Blackwell et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,763,050 B2 | 7/2010 | Winslow et al. |
| 7,763,073 B2 | 7/2010 | Hawkins et al. |
| 7,763,074 B2 | 7/2010 | Altarac et al. |
| 7,776,069 B2 | 8/2010 | Taylor |
| 7,776,090 B2 | 8/2010 | Winslow et al. |
| 7,776,091 B2 | 8/2010 | Mastrorio et al. |
| 7,789,898 B2 | 9/2010 | Peterman |
| 7,803,190 B2 | 9/2010 | Zucherman et al. |
| 7,828,822 B2 | 11/2010 | Zucherman et al. |
| 7,833,246 B2 | 11/2010 | Mitchell |
| 7,837,688 B2 | 11/2010 | Boyer, II et al. |
| 7,842,074 B2 | 11/2010 | Abdou |
| 7,846,185 B2 | 12/2010 | Carls et al. |
| 7,846,186 B2 | 12/2010 | Taylor |
| 7,862,586 B2 | 1/2011 | Malek |
| 7,862,590 B2 | 1/2011 | Lim et al. |
| 7,862,591 B2 | 1/2011 | Dewey et al. |
| 7,862,592 B2 | 1/2011 | Peterson et al. |
| 7,879,039 B2 | 2/2011 | Perez-Cruet et al. |
| 7,879,104 B2 | 2/2011 | Dewey et al. |
| 7,901,432 B2 | 3/2011 | Zucherman et al. |
| 7,909,853 B2 | 3/2011 | Zucherman et al. |
| 7,918,875 B2 | 4/2011 | Lins et al. |
| 7,918,877 B2 | 4/2011 | Zucherman et al. |
| 7,927,354 B2 | 4/2011 | Edidin et al. |
| 7,931,674 B2 | 4/2011 | Zucherman et al. |
| 7,935,133 B2 | 5/2011 | Malek |
| 7,951,151 B2 | 5/2011 | Butler et al. |
| 7,955,356 B2 | 6/2011 | Zucherman et al. |
| 7,955,357 B2 | 6/2011 | Kiester |
| 7,955,392 B2 | 6/2011 | Dewey et al. |
| 7,959,652 B2 | 6/2011 | Zucherman et al. |
| 7,985,246 B2 | 7/2011 | Trieu |
| 7,988,708 B2 | 8/2011 | Yeh |
| 7,988,709 B2 | 8/2011 | Clark et al. |
| 7,993,374 B2 | 8/2011 | Zucherman et al. |
| 7,998,173 B2 | 8/2011 | Perkins |
| 7,998,174 B2 | 8/2011 | Malandain et al. |
| 7,998,208 B2 | 8/2011 | Kohm et al. |
| 8,007,517 B2 | 8/2011 | Lins et al. |
| 8,007,521 B2 | 8/2011 | Malandain et al. |
| 8,007,537 B2 | 8/2011 | Zucherman et al. |
| 8,012,175 B2 | 9/2011 | Winslow et al. |
| 8,012,209 B2 | 9/2011 | Zucherman et al. |
| 8,021,393 B2 | 9/2011 | Seifert et al. |
| 8,021,394 B2 | 9/2011 | Butler et al. |
| 8,021,398 B2 | 9/2011 | Sweeney et al. |
| 8,025,678 B2 | 9/2011 | Reynolds et al. |
| 8,029,542 B2 | 10/2011 | Zucherman et al. |
| 8,029,549 B2 | 10/2011 | Malandain et al. |
| 8,029,550 B2 | 10/2011 | Dewey et al. |
| 8,029,567 B2 | 10/2011 | Edidin et al. |
| 8,034,079 B2 | 10/2011 | Bruneau et al. |
| 8,034,080 B2 | 10/2011 | Malandain et al. |
| 8,038,698 B2 | 10/2011 | Edidin et al. |
| 8,043,335 B2 | 10/2011 | Malandain et al. |
| 8,043,336 B2 | 10/2011 | Taylor |
| 8,043,337 B2 | 10/2011 | Klyce et al. |
| 8,043,378 B2 | 10/2011 | Stoklund et al. |
| 8,048,117 B2 | 11/2011 | Zucherman et al. |
| 8,048,118 B2 | 11/2011 | Lim et al. |
| 8,048,119 B2 | 11/2011 | Bruneau et al. |
| 8,048,128 B2 | 11/2011 | Klyce et al. |
| 8,057,513 B2 | 11/2011 | Kohm et al. |
| 8,062,337 B2 | 11/2011 | Bruneau et al. |
| 8,066,742 B2 | 11/2011 | Anderson et al. |
| 8,066,747 B2 | 11/2011 | Zucherman et al. |
| 8,070,778 B2 | 12/2011 | Zucherman et al. |
| 8,070,779 B2 | 12/2011 | Khoo |
| 8,070,780 B2 | 12/2011 | Zucherman et al. |
| 8,075,593 B2 | 12/2011 | Hess |
| 8,080,039 B2 | 12/2011 | Zucherman et al. |
| 8,083,795 B2 | 12/2011 | Lange et al. |
| 8,092,459 B2 | 1/2012 | Malandain |
| 8,092,535 B2 | 1/2012 | Zucherman et al. |
| 8,097,018 B2 | 1/2012 | Malandain et al. |
| 8,097,021 B1 | 1/2012 | Kornel |
| 8,097,038 B2 | 1/2012 | Malek |
| 8,105,358 B2 | 1/2012 | Phan |
| 8,114,132 B2 | 2/2012 | Lyons et al. |
| 8,114,136 B2 | 2/2012 | Carls et al. |
| 8,123,782 B2 | 2/2012 | Altarac et al. |
| 8,128,659 B2 | 3/2012 | Ginsberg et al. |
| 8,128,661 B2 | 3/2012 | Zucherman et al. |
| 8,142,479 B2 | 3/2012 | Hess |
| 8,147,526 B2 | 4/2012 | Auyoung |
| 8,177,813 B2 | 5/2012 | Butler et al. |
| 8,187,305 B2 | 5/2012 | Malandain et al. |
| 8,187,306 B2 | 5/2012 | Fallin et al. |
| 8,192,465 B2 | 6/2012 | Fallin et al. |
| 8,206,420 B2 | 6/2012 | Patel et al. |
| 8,216,276 B2 | 7/2012 | Trieu |
| 8,216,278 B2 | 7/2012 | Gabelberger et al. |
| 8,221,462 B2 | 7/2012 | Dwyer et al. |
| 8,221,465 B2 | 7/2012 | Trieu et al. |
| 8,221,467 B2 | 7/2012 | Butler et al. |
| 8,241,331 B2 | 8/2012 | Arnin |
| 8,246,655 B2 | 8/2012 | Jackson et al. |
| 8,246,656 B2 | 8/2012 | Ramsay et al. |
| 8,252,029 B2 | 8/2012 | Morancy-Meister et al. |
| 8,268,001 B2 | 9/2012 | Butler et al. |
| 8,273,108 B2 | 9/2012 | Altarac et al. |
| 8,277,487 B2 | 10/2012 | Nishida |

(56) References Cited

U.S. PATENT DOCUMENTS

| | | |
|---|---|---|
| 8,277,488 B2 | 10/2012 | Altarac et al. |
| 8,292,922 B2 | 10/2012 | Altarac et al. |
| 8,313,512 B2 | 11/2012 | Kwak et al. |
| 8,348,976 B2 | 1/2013 | Kohm et al. |
| 8,349,013 B2 | 1/2013 | Zucherman et al. |
| 8,372,118 B2 | 2/2013 | Chin et al. |
| 8,377,097 B2 | 2/2013 | Gordon et al. |
| 8,388,657 B2 | 3/2013 | Boyer, II et al. |
| 8,425,561 B2 | 4/2013 | Lim et al. |
| 8,480,680 B2 | 7/2013 | Lewis |
| 8,500,778 B2 | 8/2013 | Jackson et al. |
| 8,512,407 B2 | 8/2013 | Butler et al. |
| 8,523,910 B2 | 9/2013 | Seifert et al. |
| 8,591,547 B2 | 11/2013 | Smisson, III et al. |
| 2008/0021466 A1 | 1/2008 | Shadduck et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0071380 A1 | 3/2008 | Sweeney |
| 2008/0082172 A1 | 4/2008 | Jackson |
| 2008/0086212 A1 | 4/2008 | Zucherman et al. |
| 2008/0097441 A1* | 4/2008 | Hayes et al. ............ 606/64 |
| 2008/0108990 A1 | 5/2008 | Mitchell et al. |
| 2008/0114455 A1 | 5/2008 | Lange et al. |
| 2008/0161818 A1 | 7/2008 | Kloss et al. |
| 2008/0167655 A1 | 7/2008 | Wang et al. |
| 2008/0167656 A1 | 7/2008 | Zucherman et al. |
| 2008/0167657 A1 | 7/2008 | Greenhalgh |
| 2008/0177272 A1 | 7/2008 | Zucherman et al. |
| 2008/0177298 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183209 A1 | 7/2008 | Robinson et al. |
| 2008/0183211 A1* | 7/2008 | Lamborne et al. ........ 606/249 |
| 2008/0215058 A1 | 9/2008 | Zucherman et al. |
| 2008/0221692 A1 | 9/2008 | Zucherman et al. |
| 2008/0243250 A1 | 10/2008 | Seifert et al. |
| 2008/0243254 A1 | 10/2008 | Butler |
| 2008/0262619 A1 | 10/2008 | Ray |
| 2008/0281360 A1 | 11/2008 | Vittur et al. |
| 2008/0288075 A1 | 11/2008 | Zucherman et al. |
| 2008/0294199 A1 | 11/2008 | Kohm et al. |
| 2008/0294200 A1 | 11/2008 | Kohm et al. |
| 2009/0005873 A1 | 1/2009 | Slivka et al. |
| 2009/0018658 A1 | 1/2009 | Garcia |
| 2009/0062918 A1 | 3/2009 | Wang et al. |
| 2009/0105773 A1 | 4/2009 | Lange et al. |
| 2009/0118833 A1 | 5/2009 | Hudgins et al. |
| 2009/0125030 A1 | 5/2009 | Tebbe et al. |
| 2009/0138046 A1 | 5/2009 | Altarac et al. |
| 2009/0138055 A1 | 5/2009 | Altarac et al. |
| 2009/0198241 A1 | 8/2009 | Phan |
| 2009/0198245 A1 | 8/2009 | Phan |
| 2009/0198277 A1 | 8/2009 | Gordon et al. |
| 2009/0198338 A1 | 8/2009 | Phan |
| 2009/0222043 A1 | 9/2009 | Altarac et al. |
| 2009/0281628 A1 | 11/2009 | Oglaza et al. |
| 2009/0297603 A1 | 12/2009 | Joshi |
| 2009/0326592 A1 | 12/2009 | Butler et al. |
| 2010/0042151 A1 | 2/2010 | Anderson |
| 2010/0049251 A1 | 2/2010 | Kuslich et al. |
| 2010/0069961 A1 | 3/2010 | DiPoto et al. |
| 2010/0076492 A1 | 3/2010 | Warner et al. |
| 2010/0076560 A1 | 3/2010 | Weng et al. |
| 2010/0082065 A1 | 4/2010 | Butler et al. |
| 2010/0100183 A1 | 4/2010 | Prewett et al. |
| 2010/0106252 A1 | 4/2010 | Kohm et al. |
| 2010/0121381 A1 | 5/2010 | Berta et al. |
| 2010/0174316 A1 | 7/2010 | Zucherman et al. |
| 2010/0198263 A1 | 8/2010 | Siegal et al. |
| 2010/0222817 A1 | 9/2010 | Perez-Cruet et al. |
| 2010/0234889 A1 | 9/2010 | Hess |
| 2010/0249840 A1 | 9/2010 | Tanaka |
| 2010/0262188 A1 | 10/2010 | Rabiner et al. |
| 2010/0280550 A1 | 11/2010 | Reo et al. |
| 2010/0280551 A1 | 11/2010 | Pool et al. |
| 2010/0305611 A1 | 12/2010 | Zucherman et al. |
| 2011/0004248 A1 | 1/2011 | Abdou |
| 2011/0004251 A1 | 1/2011 | Sweeney et al. |
| 2011/0022090 A1* | 1/2011 | Gordon et al. ............ 606/249 |
| 2011/0022091 A1 | 1/2011 | Anderson et al. |
| 2011/0040332 A1 | 2/2011 | Culbert et al. |
| 2011/0066186 A1* | 3/2011 | Boyer et al. ............. 606/249 |
| 2011/0071568 A1 | 3/2011 | Ginn et al. |
| 2011/0077686 A1 | 3/2011 | Mishra et al. |
| 2011/0087285 A1 | 4/2011 | Khajavi et al. |
| 2011/0093013 A1 | 4/2011 | Perez-Cruet et al. |
| 2011/0098745 A1 | 4/2011 | Liu et al. |
| 2011/0098746 A1 | 4/2011 | Peterson et al. |
| 2011/0106160 A1 | 5/2011 | Altarac et al. |
| 2011/0106163 A1 | 5/2011 | Hochschuler et al. |
| 2011/0112577 A1 | 5/2011 | Zucherman et al. |
| 2011/0144692 A1 | 6/2011 | Saladin et al. |
| 2011/0160772 A1 | 6/2011 | Arcenio et al. |
| 2011/0160773 A1 | 6/2011 | Aschmann et al. |
| 2011/0166600 A1* | 7/2011 | Lamborne et al. ........ 606/249 |
| 2011/0172710 A1 | 7/2011 | Thommen et al. |
| 2011/0172711 A1* | 7/2011 | Kirschman ............... 606/252 |
| 2011/0172720 A1 | 7/2011 | Metcalf et al. |
| 2011/0178560 A1 | 7/2011 | Butler et al. |
| 2011/0190817 A1 | 8/2011 | Thommen et al. |
| 2011/0208244 A1 | 8/2011 | Shin |
| 2011/0213418 A1 | 9/2011 | Trieu et al. |
| 2011/0224731 A1* | 9/2011 | Smisson et al. .......... 606/249 |
| 2011/0264221 A1 | 10/2011 | Woodward et al. |
| 2011/0307010 A1 | 12/2011 | Pradhan |
| 2011/0307011 A1 | 12/2011 | Moskowitz et al. |
| 2011/0313458 A1 | 12/2011 | Butler et al. |
| 2011/0319935 A1 | 12/2011 | Moskowitz et al. |
| 2011/0319937 A1 | 12/2011 | Jackson |
| 2012/0016418 A1* | 1/2012 | Chin et al. ............... 606/249 |
| 2012/0016419 A1 | 1/2012 | Aflatoon |
| 2012/0089184 A1* | 4/2012 | Yeh ........................ 606/248 |
| 2012/0143252 A1* | 6/2012 | Robinson ................. 606/248 |
| 2013/0184754 A1* | 7/2013 | Taber et al. .............. 606/249 |
| 2013/0304137 A1* | 11/2013 | Zappacosta et al. ...... 606/86 A |

\* cited by examiner

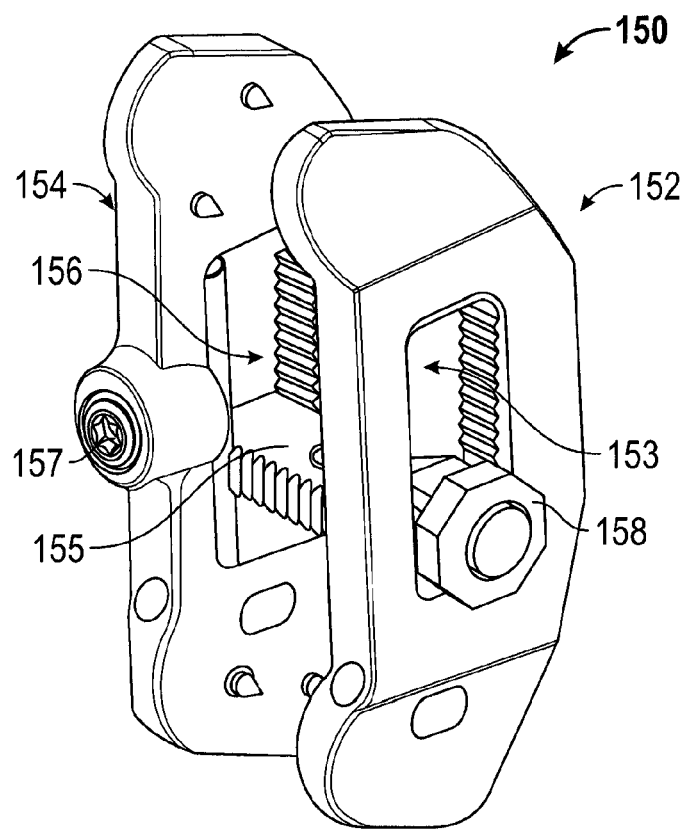
FIG. 10
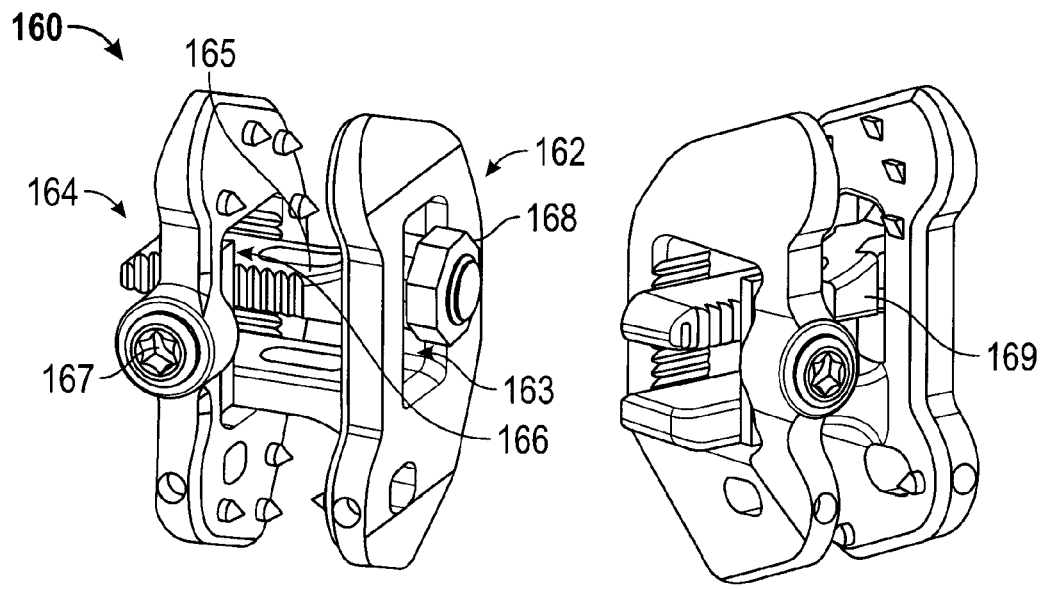
FIG. 11A  FIG. 11B

SPINOUS PROCESS DEVICE

CROSS-REFERENCE TO RELATED APPLICATION

The present application claims the priority benefit of U.S. provisional patent application No. 61/499,633, filed Jun. 21, 2011, and entitled SPINOUS PROCESS DEVICE, the entirety of which is incorporated herein by reference.

FIELD

The present disclosure generally relates to systems and methods of immobilizing vertebrae and, in particular, adjacent spinous processes to provide posterior stabilization and anatomical alignment.

BACKGROUND

Interspinous process decompression is used to treat spinal conditions such as lumbar spinal stenosis, a condition in which the spinal canal narrows and may pinch the nerve passing through the canal, or spondylolisthesis, a condition in which a spinal vertebrae is displaced from its proper position. One method of stabilizing the relative position and separation of two adjacent vertebrae is to clamp the spinous processes of the two vertebrae in position using a pair of plates that are attached to each other.

SUMMARY

One of the drawbacks to stabilizing adjacent vertebrae by clamping the spinous processes between two plates is that the plates must apply sufficient compressive force to prevent the spinous processes from slipping. This is a delicate task, as too much force presents a risk of damage to the bone of the spinous processes while too little force may allow slippage of the plates relative to one or both spinous processes, thereby allowing movement of the vertebrae. It would be desirable to provide a device that both clamps the spinous processes in place and provides a separation spacer between the spinous processes to provide a more positive restraint against closure of the gap between the vertebrae. It would be even more desirable to provide a device with an adjustable spacer such that it is not necessary to provide a variety of devices having spacers with a range of thickness. It is desirable to allow the device to be locked into position with a single action.

In some aspects, a device for immobilizing adjacent spinous processes includes a first element comprising a first surface configured to grip first sides of the adjacent spinous processes and comprising a first separation bar projecting from the first surface, a spacer element comprising an adjustment bar and a second separation bar projecting from the adjustment bar, and a second element comprising a second surface configured to grip second sides of the adjacent spinous processes and comprising a clamping feature configured to selectably fixedly lock the first separation bar and the adjustment bar.

In some aspects, a device for immobilizing adjacent spinous processes includes a first element configured to grip a first side of the adjacent spinous processes and provide a first separation bar between the spinous processes, a second element configured to grip a second opposed side of the adjacent spinous processes, a spacer element configured to provide a second separation bar between the adjacent spinous processes, and a locking feature having an unlocked configuration and a locked configuration. When the locking feature is in the unlocked configuration, the first element and the second element can undergo relative motion and the first separation bar and the second separation bar can undergo relative motion. When the locking feature is locked, the locking feature both fixes a relative position of the first element and the second element and fixes a relative position of the separation bars.

In some aspects, a method of stabilizing adjacent vertebrae having spinous processes includes the step of assembling a first element, a spacer element, and a second element into a spinous process device. The first element includes a first separation bar and a first plate having a first gripping surface, the spacer element comprising an adjustment bar and a second separation bar. The second element includes a clamping feature configured to selectably lock the first separation bar and the adjustment bar and comprising a second plate having a second gripping surface. The assembled spinous process device has the first separation bar and the adjustment bar passing through the clamping feature such that the first and second gripping surfaces are facing each other and the first and second separation bars are generally parallel to each other.

The assembled spinous process device has a first distance between the first and second gripping surfaces and a second distance between the first and second separation bars. The method also includes the step of implanting the assembled spinous process device into a patient such that the first and second gripping surfaces are disposed on opposite sides of the adjacent spinous processes and the first and second separation bars are disposed between the adjacent spinous processes.

BRIEF DESCRIPTION OF THE DRAWINGS

The accompanying drawings, which are included to provide further understanding and are incorporated in and constitute a part of this specification, illustrate exemplifying embodiments and together with the description serve to explain the principles of the disclosed embodiments. In the drawings:

FIG. 6C is a partial cross-section of the first element taken along the line C-C shown in FIG. 6B.

FIG. 10 illustrates another embodiment of a spinous process device according to certain aspects of this disclosure.

FIGS. 11A-11B are perspective views of another embodiment of a spinous process device according to certain aspects of this disclosure.

DETAILED DESCRIPTION

Figure 1:
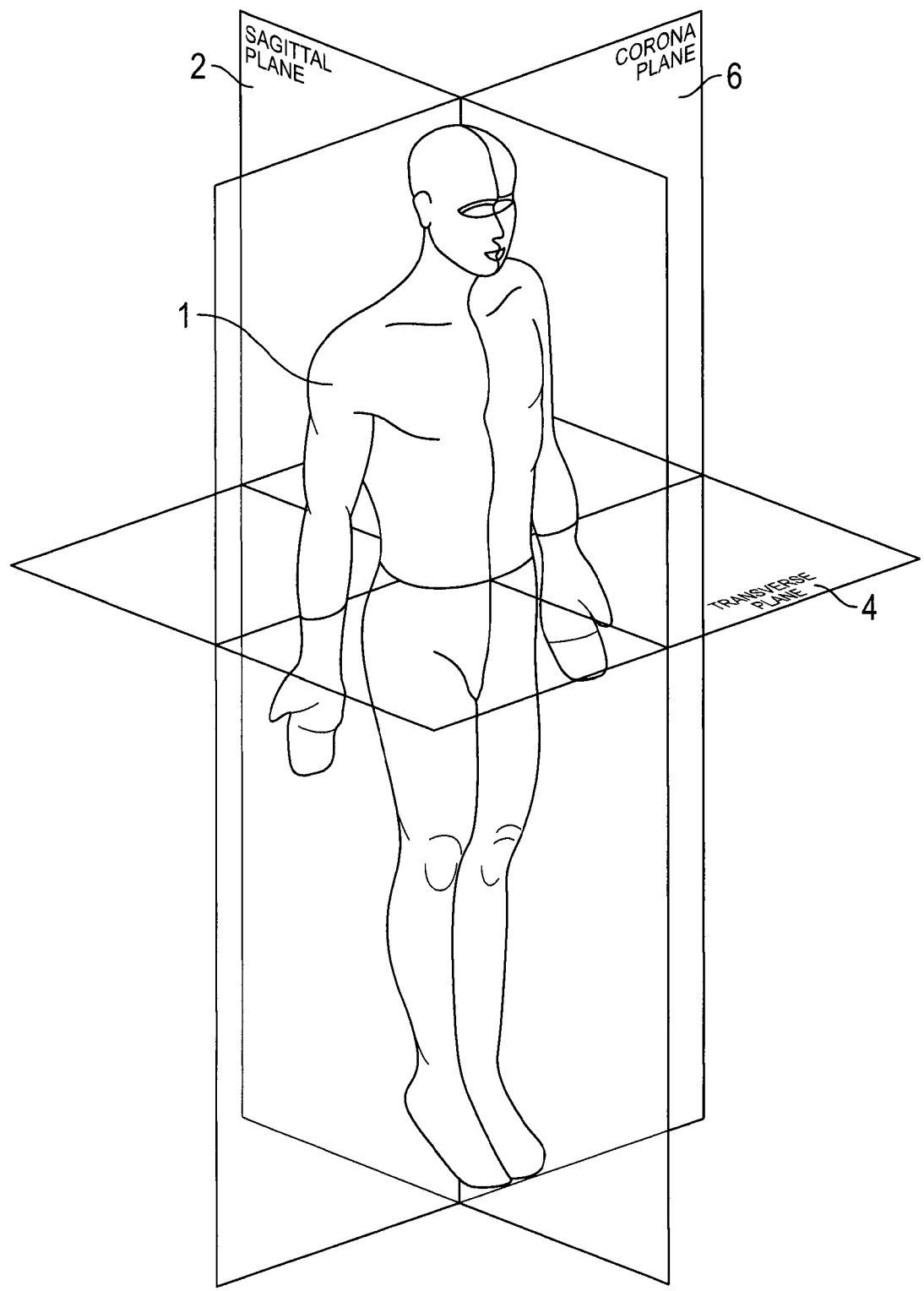
FIG. 1 is a diagram of the three reference planes of the human body.

The following description discloses embodiments of a spinous process device that provides an adjustable spacer between the spinous processes of adjacent vertebrae as well as clamping the two spinous processes between two plates so as to immobilize the vertebrae.

The disclosed system provides a spinous process device with an adjustable spacing capability. The device can be installed when there is a narrow gap between adjacent spinous processes and expanded after the spinous processes are separated to the desired positions. The result is a single device that can both provide an adjustable amount of spacing between spinous processes and then clamp the spinous processes in place.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

In the following detailed description, the phrase "continuously adjustable" means that adjustment can be made to any point within a range of adjustment rather than being restricted to selection from a set of discrete separate alternatives. For example, the relative orientation of two toothed gears engaged with each other is not continuously adjustable as the engagement of the gears must shift in increments of a full tooth. As a second example, the position of a coin lying flat on a flat horizontal tabletop can be continuously adjusted by any distance, small or large, within the bounds of the tabletop.

In the following detailed description, the term "translation" and similar terms mean movement of an item in one or more of the three spatial dimensions without rotation of the item.

In the following detailed description, the term "distraction" and similar terms mean separation of two items.

In the following detailed description, the phrase "clamping feature" means a mechanism or component that is capable of immobilizing one or more secondary elements in both translation and rotation with respect to a primary element. A clamping feature may also be referred to herein as a "locking feature" and the terms "clamp" and "lock" and the like are considered equivalent herein. A clamping feature may have a "free" or "unlocked" configuration that allows one or more of the secondary elements to move with respect to the primary element, and may also have a "clamped" or "locked" configuration wherein the secondary elements immobilize one or more secondary elements in both translation and rotation with respect to a primary element. Use of any of the terms "activating," "actuating," "locking," and the like with respect to a clamping feature means changing the configuration of the clamping feature to the locked configuration, and use of any of the terms "deactivating," "unlocking," "releasing," and the like with respect to the clamping feature means changing the configuration of the clamping feature to the unlocked configuration. Use of the phrase "moving between" and the like with respect to a clamping feature means changing the configuration of the clamping feature from one of the locked and unlocked configurations to the other of the locked and unlocked configurations.

Although various methods and systems are disclosed herein with reference to use for separating and immobilizing adjacent spinous processes, the disclosed methods and systems can be utilized in a variety of applications that require both separation and immobilization. Nothing in this disclosure should be interpreted, unless specifically stated as such, to limit the application of any method or system disclosed herein to spinous processes.

FIG. 1 is a diagram of the three reference planes of the human body 1. These three planes include the coronal, or frontal, plane 6, which passes from left to right through the body. The sagittal, or lateral, plane 2 passes from front to back. The transverse, or axial, plane 4 passes horizontally through the body 1 of a standing person.

Figure 2A:
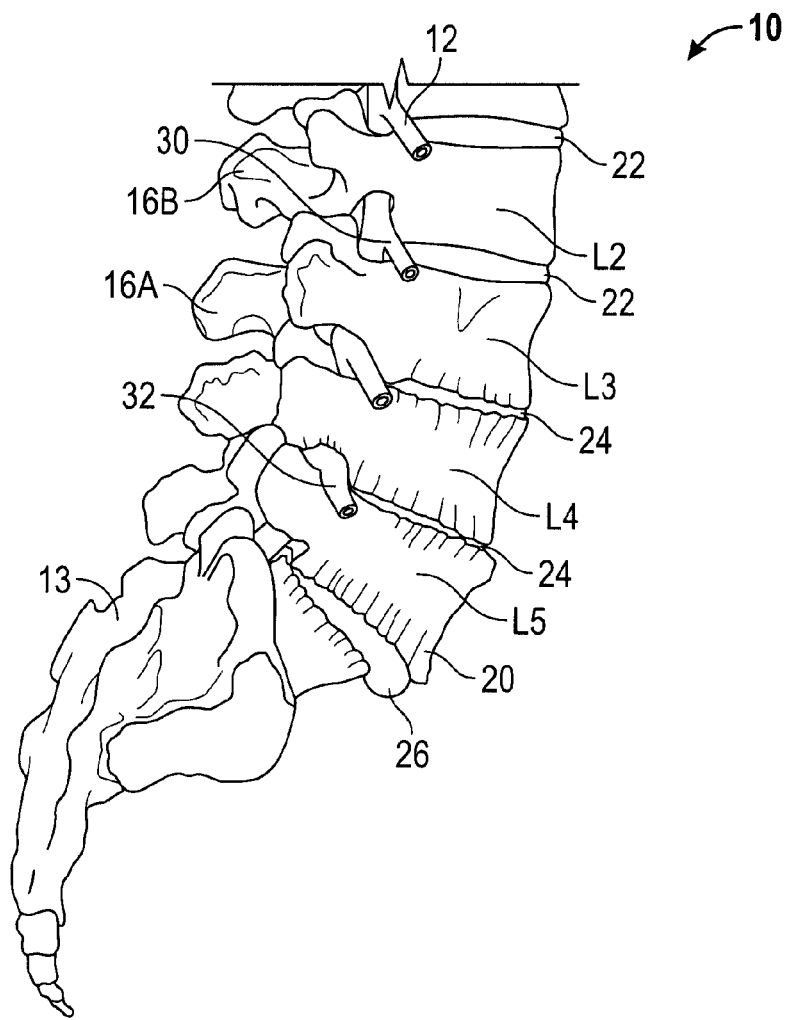
FIG. 2A is a side view of a portion of a human spine illustrating certain conditions.

FIG. 2A is a side view of a portion of a human spine 10 illustrating certain conditions. This portion includes the lumbar vertebrae L2-L5 and the sacrum 13. Each vertebra 20 has a central flange 16 that is called a "spinous process." In this example, vertebra L3 has a spinous process 16A and vertebra L2 has a spinous process 16B that is adjacent to spinous process 16A. Healthy intervertebral discs 22 are shown between vertebrae L2 and L3 and compressed discs 24 are shown between vertebrae L3 and L4 and between vertebrae L4 and L5. The spinal cord 12 passes through openings in the vertebrae and a healthy spinal nerve 30 is shown branching off from the spinal cord 12 and passing between vertebrae L2 and L3. The compression of disc 24 between vertebrae L4 and L5 has narrowed the gap through which the spinal nerve 32 is passing thereby pinching spinal nerve 32, a condition called lumbar spinal stenosis. The L5 vertebra, in this example, is displaced from its normal position, a condition called spondylolisthesis. This has resulted in the disc 26 becoming squeezed toward one side and, as can be seen, the disc 26 is bulging outward compared to the healthy discs 22.

Figure 2B:
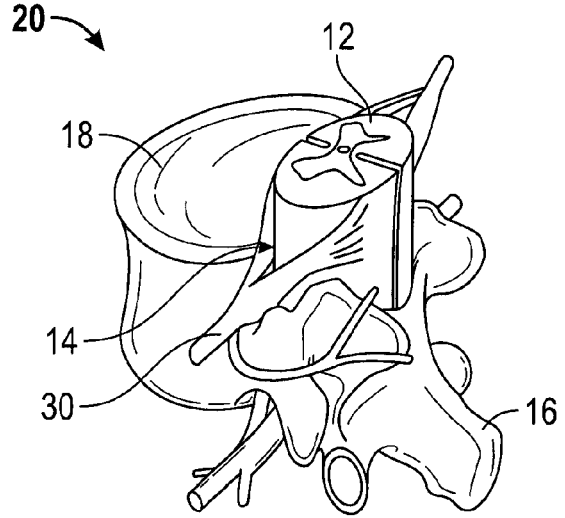
FIG. 2B is a perspective view of a single human spinal vertebrae and the nearby spinal cord and nerves.

FIG. 2B is a perspective view of a single human spinal vertebra 20 and the nearby spinal cord 12 and nerves 30. The vertebra 20 includes a body 18 and a central spinous process 16, with the spinal nerve 30 passing through a gap 14.

Figure 3A:
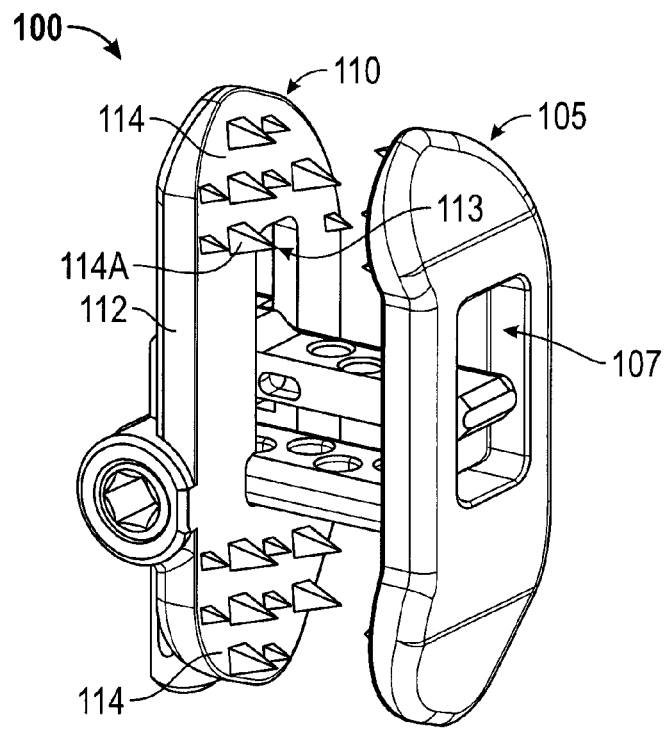
FIGS. 3A-3B are perspective views of an exemplary embodiment of the spinous process device according to certain aspects of this disclosure.
Figure 3B:
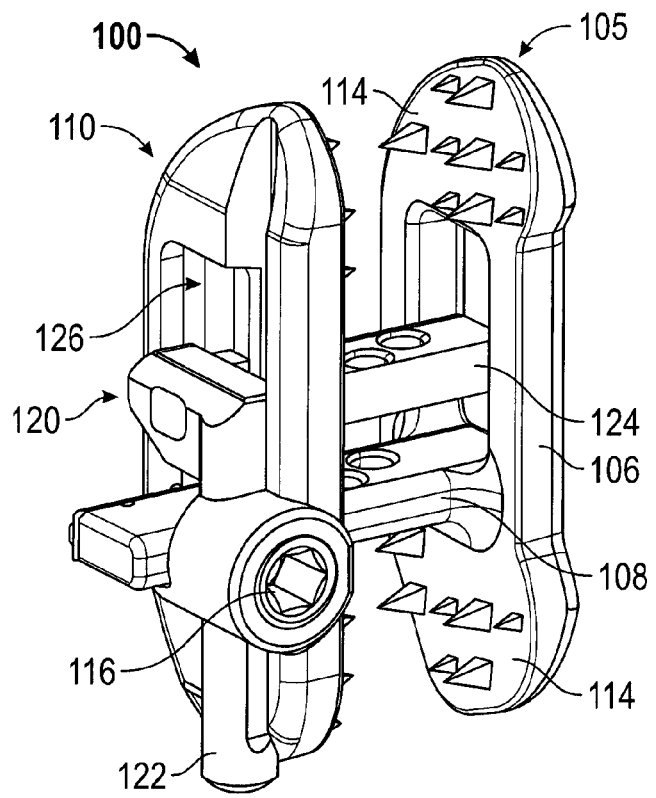

FIGS. 3A-3B are perspective views of an exemplary embodiment of a spinous process device 100 according to certain aspects of this disclosure. The device 100 may comprise a first element 105 comprising a first plate 106 configured to overlap one of the left and right sides of the adjacent spinous processes 16, for example spinous processes 16A and 16B of FIG. 2A. The first plate 106 may have two gripping sides that each have gripping surfaces 114 and a first separation bar 108 fixedly coupled to the first plate 106 and projecting approximately orthogonal to the gripping surfaces 114. The device 100 may also include a spacer element 120 comprising an adjustment bar 122 and a second separation bar 124 fixedly coupled to the adjustment bar 122 and projecting approximately orthogonal to the adjustment bar 122. The device 100 may also include a second element 110 comprising a second plate 112 configured to overlap the other of the left and right sides of the adjacent spinous processes 16. The second plate 112 may have gripping surfaces 114 and a receptacle 117 (FIG. 6A) configured to accept the first separation bar 108. The second element 110 may also have a channel 126 configured to slidably accept the spacer element 120 such that the second separation bar 124 projects approximately orthogonal to the gripping surface(s) 114 of the second element 110. The second element 110 may also include a clamping, or locking, feature 116 coupled to the plate 112. The clamping feature 116 is configured to loosely capture one or both of the adjustment bar 122 and the separation bar 108 when the clamping feature is in an unlocked configuration and to lock both the adjustment bar 122 and the separation bar 108 when the clamping feature 116 is actuated. The clamping feature 116 is discussed in greater detail with respect to FIGS. 6A-6C.

The gripping surfaces 114 of first and second elements 105, 110 may each include one or more surfaces. For example, in the embodiment 100 of FIGS. 3A and 3B, spikes 114A are disposed over a portion of the gripping side. As illustrated in this example, the spikes 114A can have multiple facets and be formed in the shape of pyramids of various heights. In some embodiments, these spikes 114A may have other shapes, such as cones, hemispheres, planar teeth, and such. When gripping a spinous process 16, or other feature to be immobilized, the some or all of the spikes 114A, e.g. tips of the spikes, may penetrate the spinous process 16 such that only a portion of the spikes 114A are in contact with the spinous process 16. Smaller spikes 114A and the flat surface to which the spikes 114A are joined may contact the spinous process 114 in some instances, but not others. The gripping surface 114 can comprise the facets of spikes 114A. In some instances, the spinous process 16 may contact only a portion of the gripping surface 114.

One aspect of the spinous process device 100 of FIGS. 3A and 3B is that the separation bars 108 and 124 have a distance between them that is adjustable. Separation bars 108 and 124 can be brought close together to provide a low profile cross element that can be introduced into a minimum of space between spinous processes 16 of adjacent vertebrae 20. This may facilitate placement of the spinous process device 100 as the shape of spinous processes 16 creates a reduced gap between the tips of adjacent spinous processes 16 when the spacing between adjacent vertebrae is reduced, as shown in FIG. 2A for vertebrae L4 and L5. This may be particularly advantageous when adjacent vertebrae 20 have shifted or an inter-vertebral disk 24 has collapsed and the space between the adjacent spinous processes 16 is less than normal. In other situations, the separation bars 108 and 124 can be distracted, i.e. separated, such as when the implant 10 is in place within the larger gap between adjacent spinous processes 16 closer to the body 18 of vertebrae 20, or when the spinous processes 16 themselves have been separated, or to cause the spinous processes 16 to separate. The distance between first element 105 and second element 110 may also be adjustable.

Figure 7:
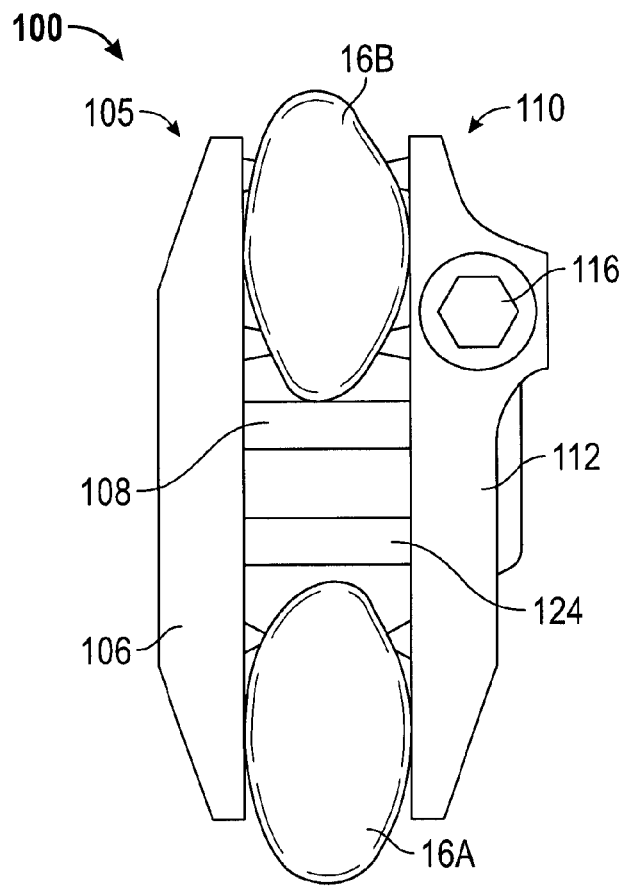
FIGS. 7 and 8 illustrate how the two elements of the device of FIGS. 4A-4D adjust while clamping adjacent spinous processes.
Figure 8:
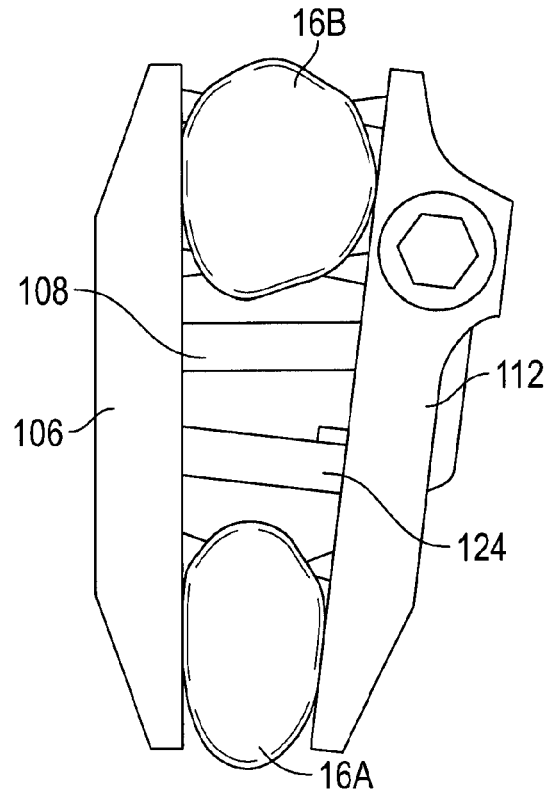

First element 105 may have a window 107 therethrough suitable for separation bar 124 to pass through. Second element 110 may have a window 113 therethrough suitable for one or both of separation bar 108 and separation bar 124 to pass through. Such windows may have sufficiently close clearance with respective separation bars 108, 124 so as to limit certain degrees of freedom of motion, such as rotation, or alternatively may have a more wide-open clearance. Second element 110 may have receptacle 117, which may comprise a specially shaped contour of a portion of the window through second element 110. Receptacle 117 may have a shape that may be complementary in shape to separation bar 108, such as a portion of a rounded rectangle for example, and have a desired clearance with respect to separation bar 108. Second element 110 may have channel 126, which may extend in a direction generally from spinous process 16A to spinous process 16B when arranged as shown in FIGS. 7 and 8 for example. Channel 126 may be configured to receive and guide adjustment bar 122. Adjustment bar 122 may have, in at least some places, a cross-sectional shape that is non-circular such as having a flat 123. Such shape may serve either to limit rotation of adjustment bar 122 or to provide a flat space upon which clamping feature 116 such as a setscrew may bear. Adjustment bar 122 and separation bar 124 or both may cooperate with channel 126 to guide or limit the motion of adjustment bar 122 and separation bar 124, such as to limit rotation thereof about any axis. Nevertheless, it is possible that a desired amount of rotation in certain directions may be allowed. Adjustment bar 122 may be approximately perpendicular to separation bar 124 although this is not essential. The adjustment bar 122 and the separation bar 124 can be arranged in some embodiments such that angles greater or less than 90 degrees are formed between them.

Figure 6A:
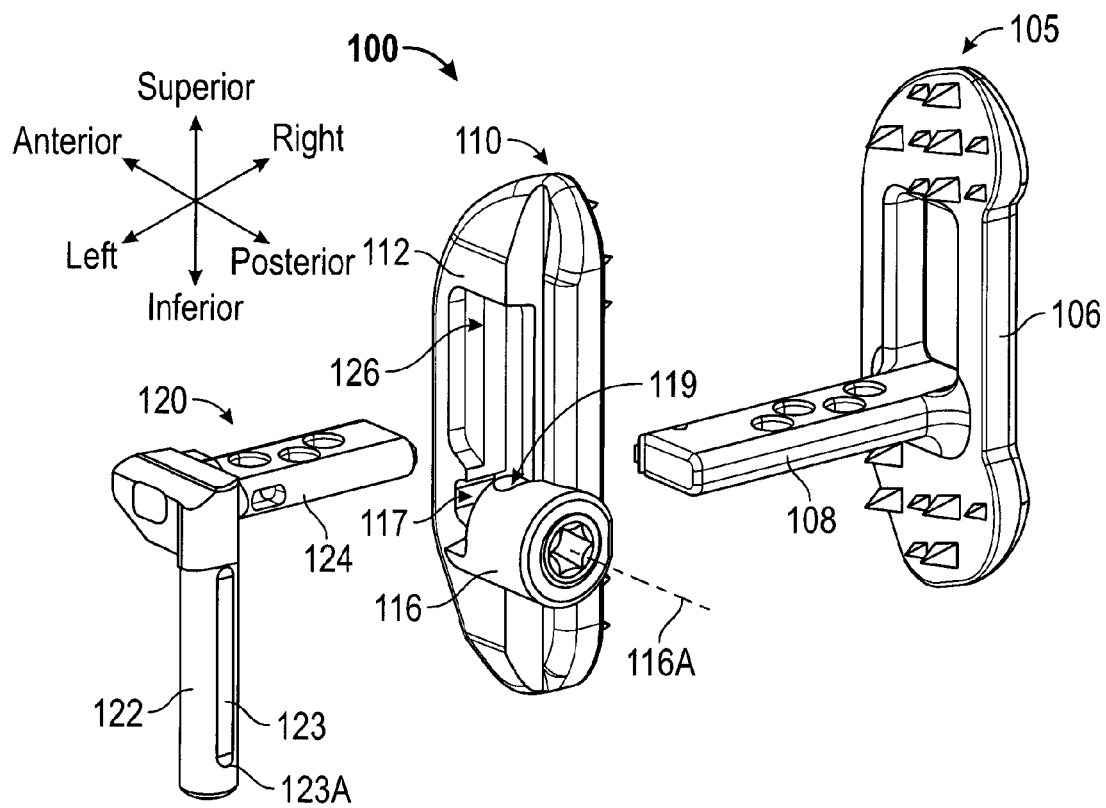
FIG. 6A is an exploded view of the device of FIGS. 3A-3B according to certain aspects of this disclosure.
Figure 6B:
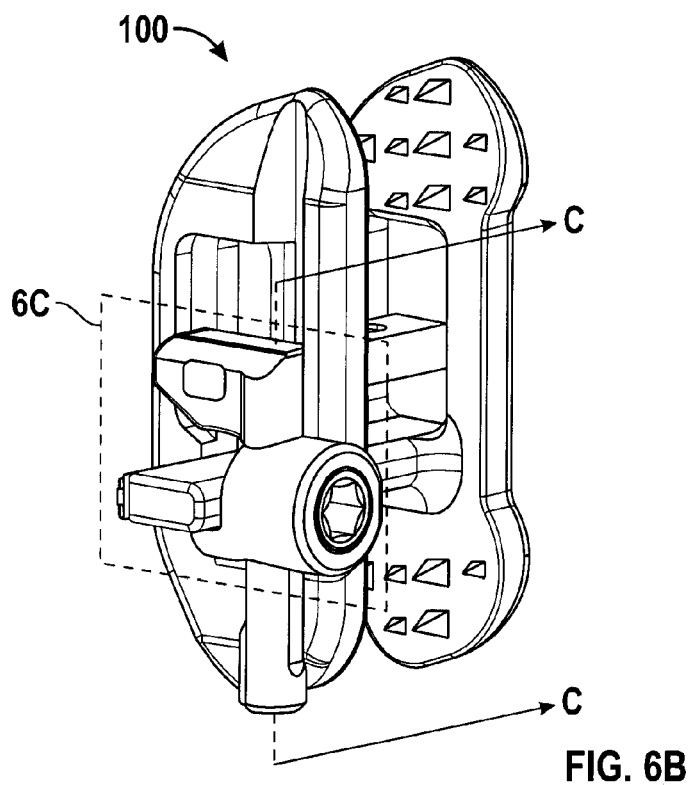
FIGS. 6B-6C depict an exemplary clamping feature of the first element of the spinous process device according to certain aspects of this disclosure.
Figure 6C:
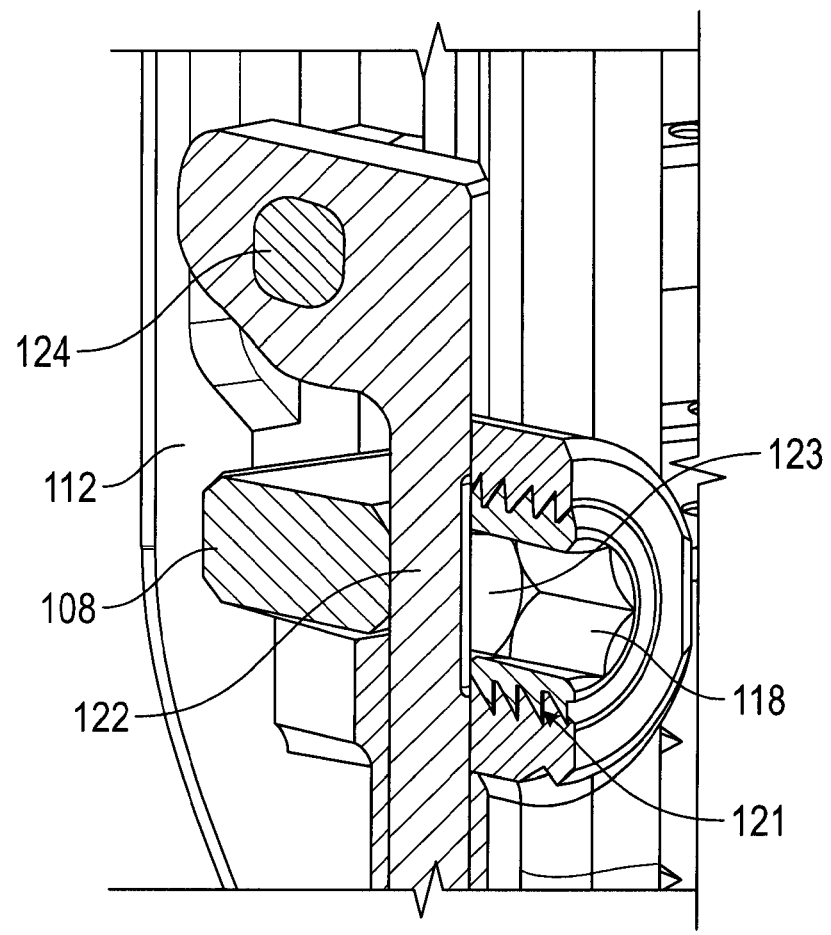

As illustrated in one of FIGS. 6A-6C for example, clamping feature 116 may comprise a through-hole 119 through which adjustment bar 122 may fit, and may comprise a hole 121 that accepts a setscrew 118, and the hole 119 and the through-hole 121 may intersect. Various components may have features that prevent disassembly. For example, adjustment bar 122 may have at one end a feature that prevents adjustment bar 122 from sliding completely through clamping feature 116. Such feature may arise from the feature that flat 123 may extend for less than the full length of adjustment bar 122. For example, the flat 123 can terminate at a location 123A that is spaced from an end of the adjustment bar 122. Separation bar 124 may have at its end a feature that prevents it from sliding through first element 105. Separation bar 108 may have at its end a feature that prevents it from sliding through second element 110. Any surface of any component that bears against another surface when the clamping feature 116 is in its locked configuration may be textured in some embodiments.

Either or both of separation bars 108, 124 may have a slot or one or more holes therethrough, which may be oriented in a direction that is generally parallel to the direction from spinous process 16A to spinous process 16B when the device and spinous processes are arranged as shown in FIGS. 7 and 8. Such hole(s) or slot may be suitable to allow growth of bone therethrough. First element 105 and second element 110 may have gripping surfaces 114, which may comprise any of various forms of spikes, ridges, grooves, roughness, and similar features and combinations thereof to aid in gripping bone, such as spinous processes 16. Adjustment bar 122 and separation bar 124 may be either joined to each other after separate manufacture or manufactured integrally with each other. First element 105 and separation bar 108 may be either joined to each other after separate manufacture or manufactured integrally with each other.

FIGS. 4A-4D illustrate an exemplary insertion tool 200 for use with the spinous process device 100 of FIGS. 3A-3B according to certain aspects of this disclosure. The illustrated tool 200 comprises a first arm 210 configured to engage one of the first and second elements 105, 110 of the device 100 and a second arm 220 coupled to the first arm 210. The second arm 220 is configured to engage the other of the first and second elements 105, 110 of the device 100. In certain embodiments, the first and second arms 210, 220 are configured to hold the first and second elements 105, 110 approximately parallel to each other at a first separation distance and, when actuated, to displace the first and second elements 105, 110 towards each other. In certain embodiments, the first and second arms 210, 220 are configured to hold the first and second elements 105, 110 at an angle to each other within an angular range and to selectably adjust an average distance between the first and second elements 105, 110. The tool 200 can also include a third arm 230 coupled to one of the first and second arms 210, 220. The third arm 230 is configured to selectably separate the first and second separation bars 108, 124.

Figure 4A:
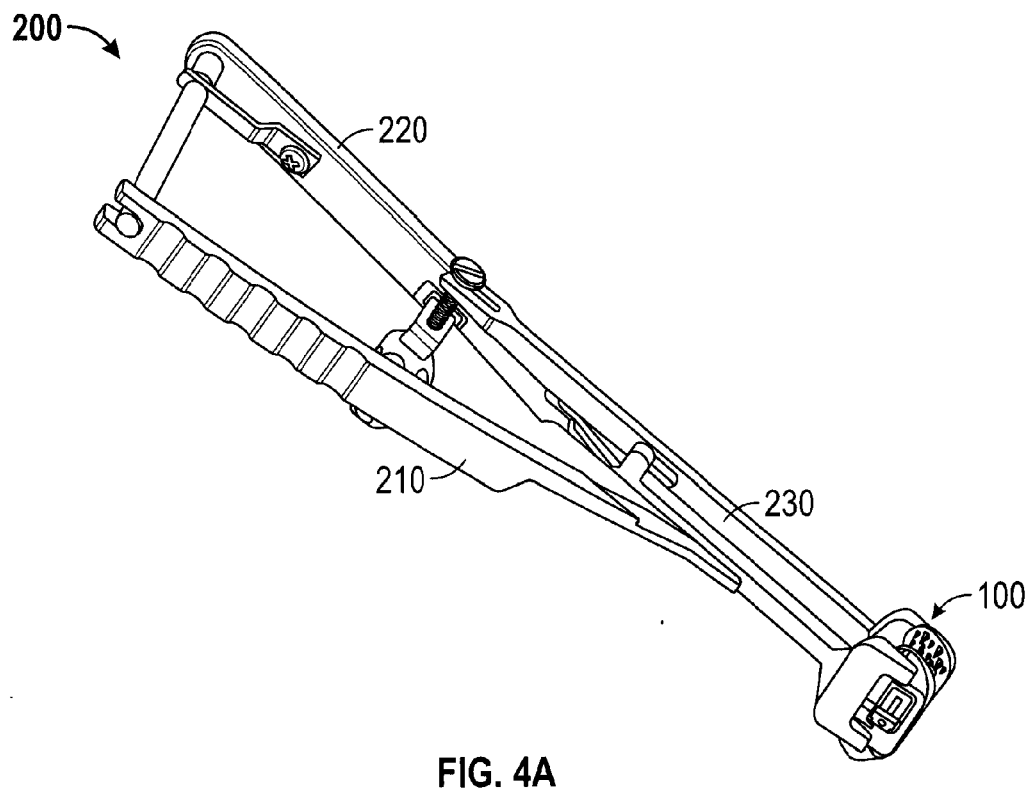
FIGS. 4A-4D illustrate an exemplary insertion tool for use with the device of FIGS. 3A-3B according to certain aspects of this disclosure.
Figure 4B:
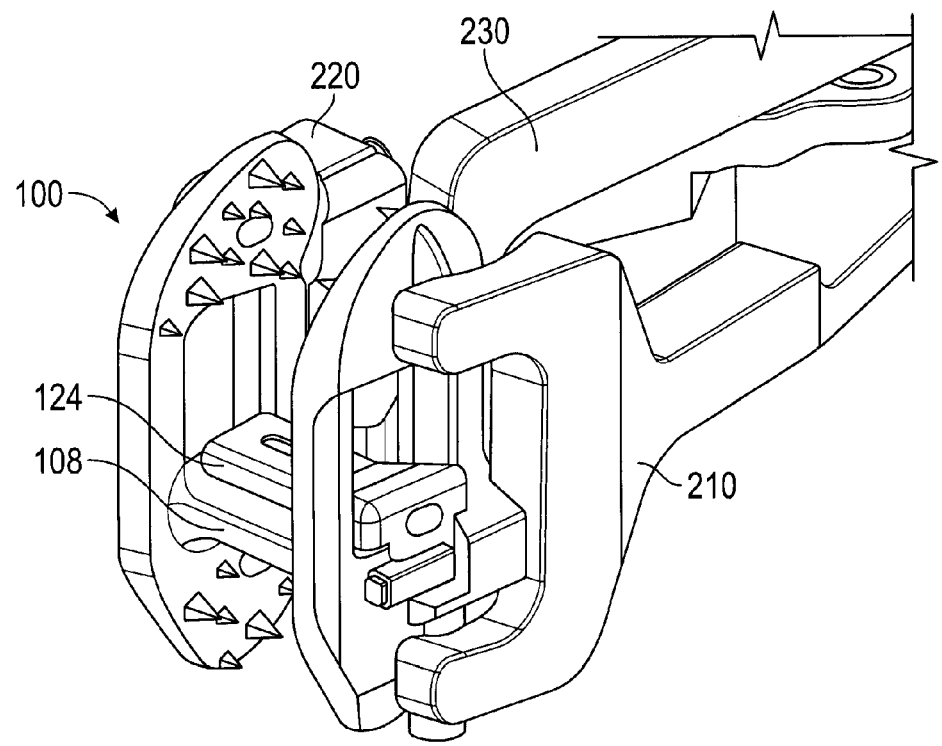

FIG. 4B provides an enlarged view of the engagement of the tool 200 with a spinous process device 100 from a reverse angle. The first and second arms 210, 220 can be seen to have C-shaped ends that engage features, e.g. holes in the first and second plates 106, 122.

Figure 4C:
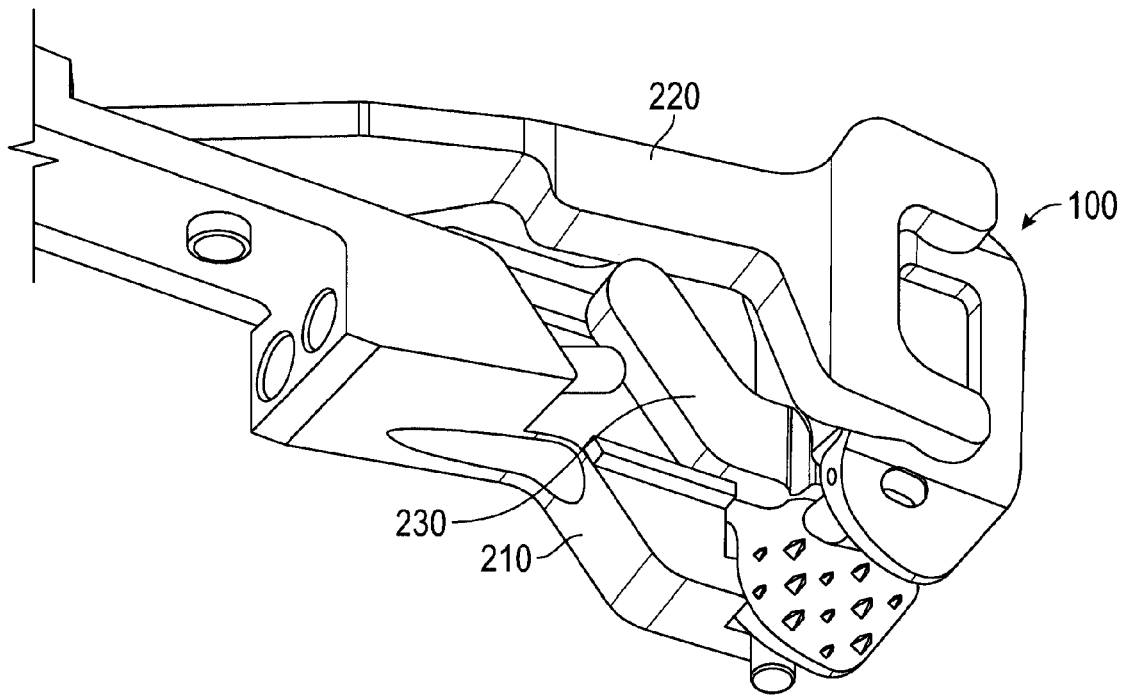

FIG. 4C is an enlarged view of the engagement of the tool 200 with a spinous process device 100 from yet another angle that makes visible the engagement of third arm 230 with the first and second separation bars 108, 124. Rotation of the third arm 230 will move the separation bar 124 of spacer element 120 away from the separation bar 108.

Figure 4D:
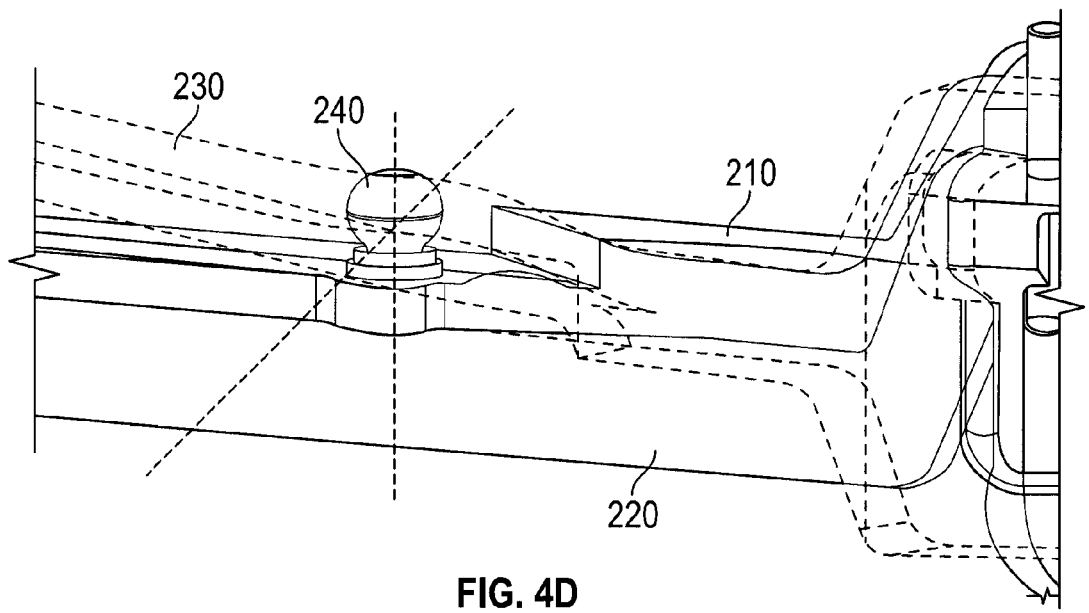

FIG. 4D illustrates the quasi-spherical joint 240 between the first and second arms 210, 220 that, in this embodiment, allows the arms to rotate with respect to each other not only about a vertical axis, as seen in this view, through the joint 240 but also around a longitudinal axis generally aligned with the long dimensions of the two arms 210, 220. This allows the first and second elements 105, 110 to rotate relative to each other as they are brought together to clamp the spinous processes at an angle, as shown in FIGS. 7 and 8.

Figure 5A:
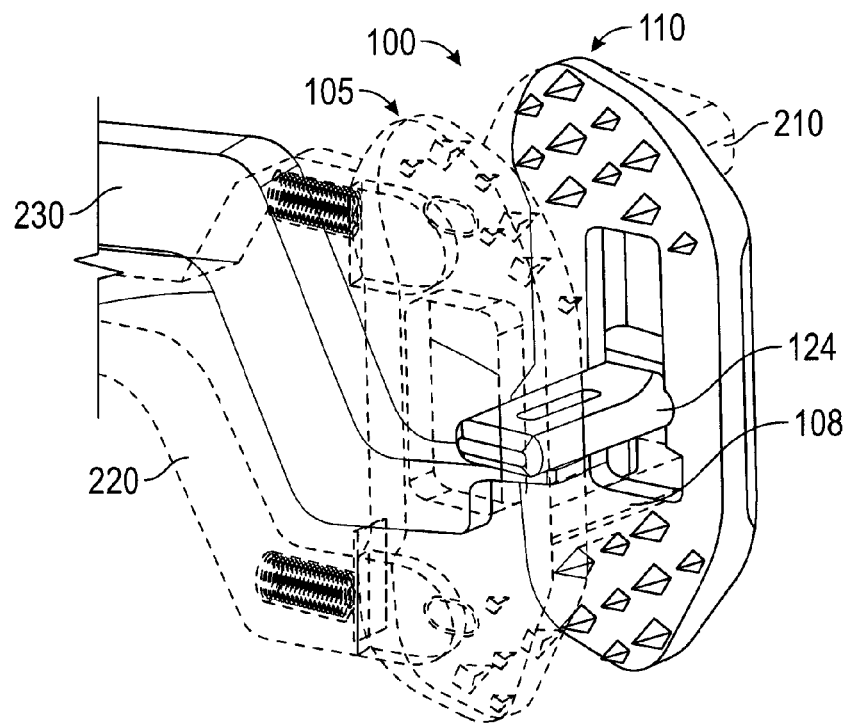
FIGS. 5A-5B illustrate the operation of the tool of FIGS. 4A-4B to increase the separation of the two separation bars of the device of FIGS. 4A-4D.
Figure 5B:
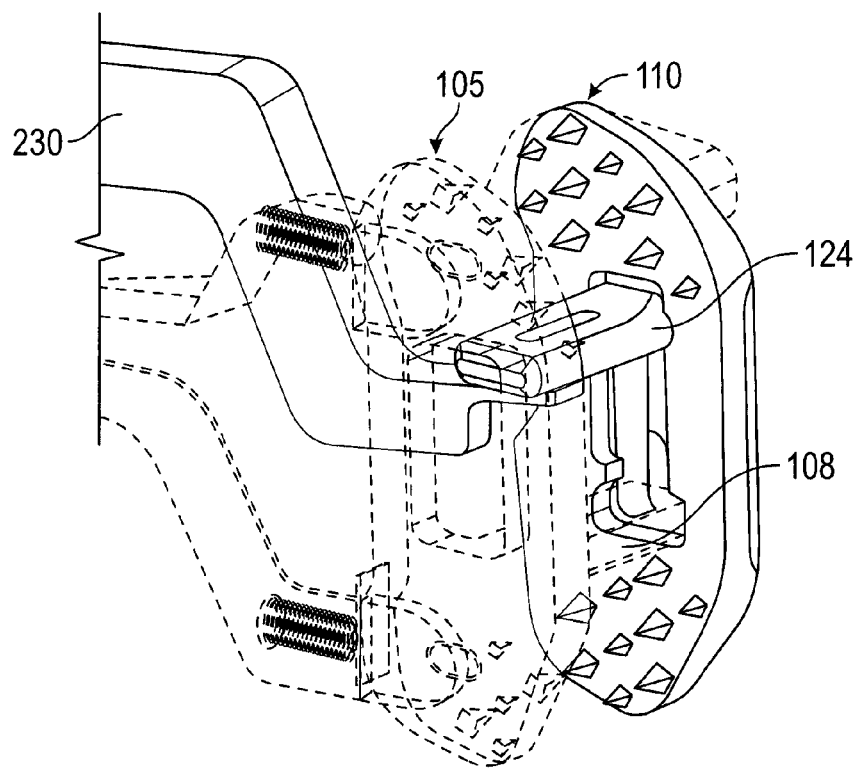

FIGS. 5A-5B illustrate the operation of the tool of FIGS. 4A-4B to increase the separation of the two separation bars of the device of FIGS. 4A-4D. FIG. 5A illustrates the configuration of device 100 and tool 200 after placing the first element 105 proximate to adjacent spinous processes 30 with the separation bar 108 passing through a gap between the adjacent spinous processes (not shown in FIGS. 5A-5B) and placing the second element 110 proximate to the adjacent spinous processes such that the separation bar 108 is accepted by the receptacle, and also placing the spacer element 120 such that the separation bar 124 passes through the gap between the adjacent spinous processes and the adjustment bar 122 is accepted by a channel 126 in the second element 110.

FIG. 5B illustrates the configuration of the device 100 and tool 200 sliding the spacer element 120 relative to the second element 110 such that the separation of the separation bars 108, 124 is increased. The clamping feature 116 of the second element 110 would be activated in the configuration of FIG. 5B to clamp or lock both the adjustment bar 122 and the separation bar 108.

In certain embodiments, the device 100 is not used to distract, or separate, the two spinous processes 16. The device 100 is installed in a collapsed configuration for ease of insertion and then expanded to fill a gap previously created by the surgeon between the adjacent spinous processes 16. In certain embodiments, the device 100 is inserted between the spinous processes 16 prior to distraction, the two spinous processes 16 are then distracted using a different tool (not shown), and the device 100 expanded.

In certain embodiments, the device 100 is used to provide the distraction of the spinous processes 16. The device 100 may be inserted installed in a collapsed configuration between adjacent spinous processes 16 using the tool 200. The tool 200 may then be manipulated to distract the separation bars 108 and 124 and thereby distract the adjacent spinous processes 16. In certain embodiments, the tool 200 may be used to assist the operation of a different distraction tool (not shown).

FIG. 6A is an exploded view of the device 100 of FIGS. 3A-3B according to certain aspects of this disclosure. In this view, the receptacle 117 that accepts the first separation bar 108 is visible. The adjustment bar 122 comprises a flat 123. An axis 116A is defined for the clamping, or locking, feature 116.

FIG. 6A also includes a set of reference axes and general directions that are appropriate for a typical orientation of the spinous process device 100 when used to stabilize adjacent spinous processes 16. The superior-inferior axis, the posterior-anterior axis, and the left-right axis are oriented perpendicular to each other. The axes are provided solely for convenience in discussion of directions of the orientation of various elements and features of the spinous process device 100 within this application. Depiction of any device, or any element or feature thereof, does not restrict the possible positions or orientations of the device, element, or feature and does not restrict the use of any device to an orientation disclosed herein. Discussion of an orientation of an element or feature making reference to these axes does not imply that element or feature is restricted to this orientation. With respect to the exemplary spinous process device 100 in a configuration oriented as shown in FIG. 6A, the longest dimensions of elements 105, 110 are generally parallel with the superior-inferior axis, the longest dimensions of the separation bars 108, 124 are generally parallel with the left-right axis, and the axis 116A is generally parallel to the posterior-anterior axis.

FIGS. 6B-6C depict an exemplary clamping feature 116 of the first element 112 of the spinous process device 100 according to certain aspects of this disclosure. FIG. 6B shows the complete device 100 with a section-line C-C and a dashed-line box "6C" indicating the portion of a cross-sectional view of device 100 that is enlarged in FIG. 6C.

FIG. 6C is a partial cross-section through the spinous process device 100 along line C-C showing the clamping feature 116. The illustrated clamping feature 116 has a set screw 118 that bears on the flat 123 of the adjustment bar 122 of the spacer element 120. In the locked configuration, setscrew 118 may bear against adjustment bar 122, such as against flat 123 of adjustment bar 122, and adjustment bar 122 in turn may bear against separation bar 108, which in turn may bear against a surface of second element 110 such as receptacle 117. There may be sufficient clearance between the second separation bar 124 and the second plate 112 to allow the adjustment bar 122 to be displaced laterally by advancement of the set screw 118, thereby applying pressure to the first separation bar 108 which bears against the second plate 112. Thus, tightening of the set screw 118 can lock both the adjustment bar 122 and the first separation bar 108. As the adjustment bar 122 is fixedly coupled to the second separation bar 124, the single action of tightening set screw 118 locks both separation bars 108, 124 in their relative positions and further locks both plates 106, 112 in their relative positions.

FIGS. 7 and 8 illustrate how the two elements 105, 110 of the device 100 of FIGS. 4A-4D adjust while clamping adjacent spinous processes 16A, 16B. In FIG. 7, the two plates 106, 112 are approximately parallel and therefore the separation bars 108, 124 are also approximately parallel.

In FIG. 8, with reference to the spinous processes identified in FIG. 2A, the lower spinous process 16A is thinner in the area gripped by the plates 106, 112 that the upper spinous process 16B. To apply equal pressure to both spinous processes 16A, 16B, the two plates 106, 112 rotate with respect to each other as they are brought together. The separation bars 108, 124 remain approximately perpendicular, in this embodiment, to the respective plates 106, 112. The spacer element 120 can still be moved, however, in the channel 126 of the element 110 so that both separation bars 108, 124 are in contact with the respective spinous processes 16A, 16B. As the first separation bar 108 passes through the clamping feature 116 at an angle, tightening of the set screw 118 locks both the first separation bar 108 and the adjustment bar 122. When the clamping feature 116 is unlocked, the separation bars 108 and 124 can be either parallel to each other or non-parallel to each other, and the plates 106, 112 can be either parallel to each other or non-parallel to each other. When the clamping feature 116 is locked, the separation bars 108 and 124 can be either parallel to each other or non-parallel to each other, and the plates 106, 112 can be either parallel to each other or non-parallel to each other. Thus, in some embodiments, the device 100 is capable of being locked in either a configuration wherein the plates and/or separation bars are parallel or in a configuration wherein they are nonparallel.

Figure 9A:
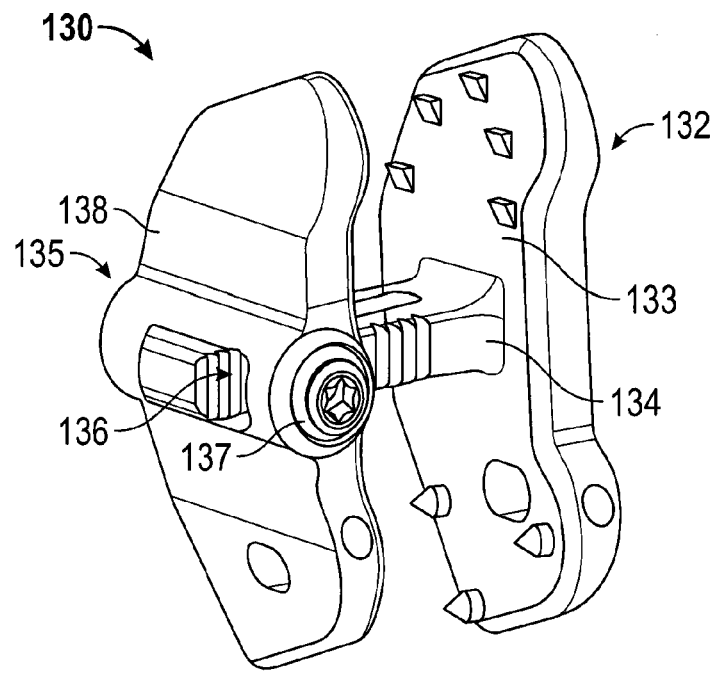
FIG. 9A illustrates another embodiment of a spinous process device according to certain aspects of this disclosure.

FIG. 9A illustrates another embodiment of a spinous process device 130 according to certain aspects of this disclosure. The device 130 has a first element 132 with a connection bar 134 that projects orthogonally from a gripping plate 133. The device 130 also has a second element 135 with a second gripping plate 138 with a passage 136 configured to receive the connection bar 134. Element 135 also has a clamping feature 137 configured to clamp or lock the connection bar 134 when actuated.

Figure 9B:
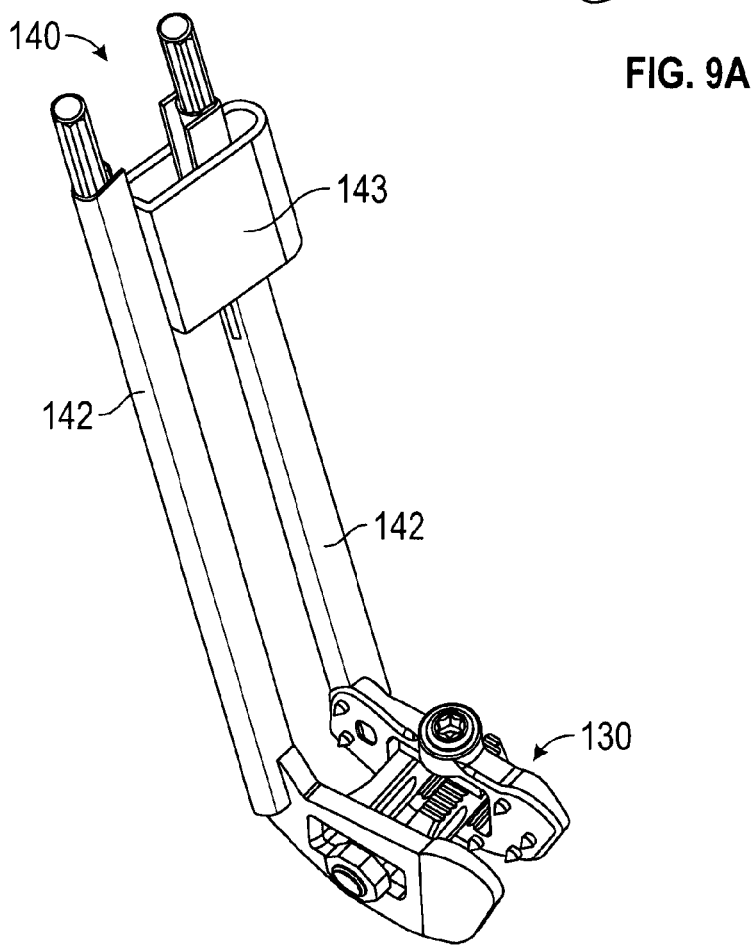
FIG. 9B illustrates an insertion tool adapted for use with the device of FIG. 9A according to certain aspects of this disclosure.

FIG. 9B illustrates an insertion tool 140 adapted for use with the device 130 of FIG. 9A according to certain aspects of this disclosure. The tool 140 has two handles 142 that couple to the first and second elements 132, 135 of device 130. The tool 140 also includes an alignment block 143 that assists in providing the proper spacing of the first and second elements 132, 135 as the second element 135 is introduced during implantation.

FIG. 10 illustrates another embodiment of a spinous process device 150 according to certain aspects of this disclosure. The device 150 has a first element 152 with a slot 153 and a second element 154 with a slot 156. A connection bar 155 is configured to bridge the distance between elements 152, 154. A nut 158 is attached to the connection bar 155 at one end, wherein the connection bar 155 includes a feature (not visible in FIG. 10) that locks the connection bar to the slot 153 when the nut 158 is tightened. The second element 154 has a clamping feature 157 that locks the other end of connection bar 155 to the slot 156 when the clamping feature 157 is actuated.

It can be seen that the rear interior surfaces of slots 153, 156 have horizontal grooves. The mating rear surface (not visible in FIG. 10) of connection bar 155 has complementary horizontal grooves. The front surface of connection bar 155 can be seen to have vertical grooves and the mating rear surface (not visible in FIG. 10) of clamping feature 157 has complementary vertical grooves. Then the clamping feature 157 is tightened, the vertical grooves on the back of the clamping feature 157 engage the vertical grooves of the connection bar 155 and displace connection bar 155 such that the horizontal grooves on the back of the connection bar 155 engage the horizontal grooves on slot 156, thereby locking the connection bar 155 into a fixed position in both the vertical and horizontal directions with respect to the second element 154. The front interior surface (not visible in FIG. 10) of slot 153 does not have grooves. Tightening of the nut 158, after the clamping feature 157 is tightened, draws the first element 152 toward the second element 154 until the spinous processes 16 (not shown in FIG. 10) are clamped between the elements 153, 154, whereupon further tightening of the nut 158 provides clamping pressure on the spinous processes 16.

FIGS. 11A-11B are perspective views of another embodiment of a spinous process device 160 according to certain aspects of this disclosure. The device 160 has a first element 162 with a slot 163 and a second element 164 with a slot 166. A connection bar 165 is configured to bridge the distance between elements 162, 164. A nut 168 is attached to the connection bar 165 at one end, wherein the connection bar 165 includes a feature 169 that locks the connection bar 165 to the slot 163 when the nut 168 is tightened. The second element 164 has a clamping feature 167 that locks the other end of connection bar 165 to the slot 166 when the clamping feature 167 is actuated. Slot 166, connection bar 165, and clamping feature 167 have grooves disposed similar to those of device 150 in FIG. 10, and tightening of clamping feature 167 followed by tightening of nut 168 will accomplish locking and clamping actions similar to those described for device 150.

Figure 12A:
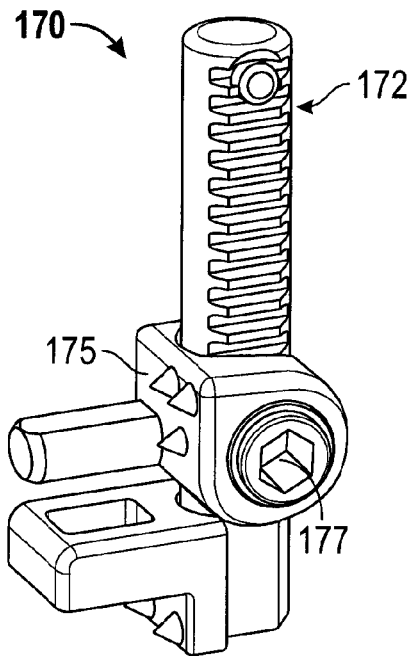
FIGS. 12A-12C are perspective views of another embodiment of a spinous process device according to certain aspects of this disclosure.
Figure 12B:
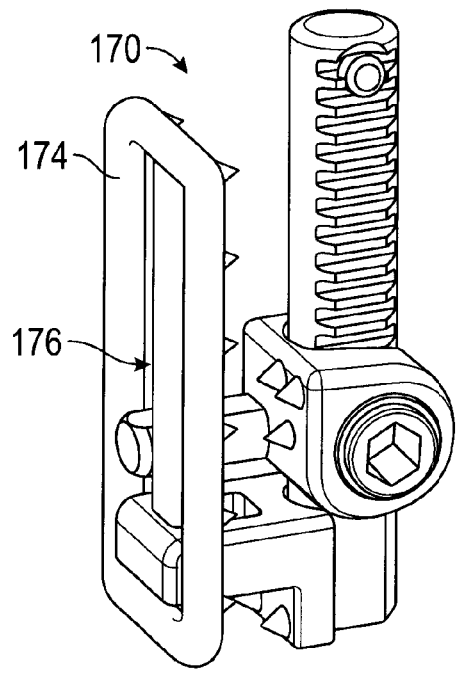
Figure 12C:
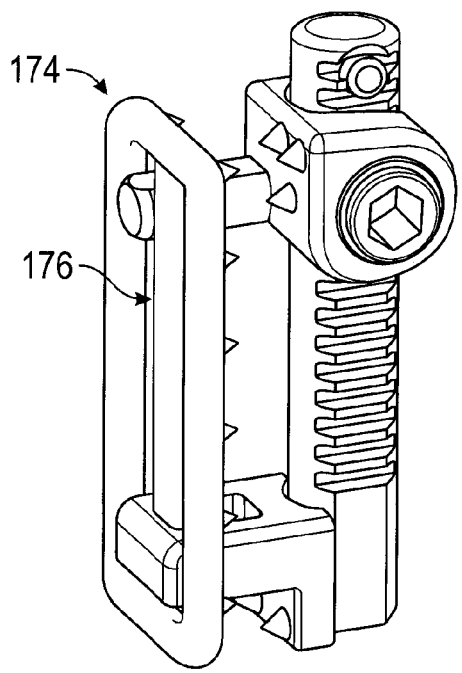

FIGS. 12A-12C are perspective views of another embodiment of a spinous process device 170 according to certain aspects of this disclosure. The device 170 has a first element 172 and a second element 174 with a slot 176. A connection bar 175 is configured to bridge the distance between elements 172, 174 and fit into the slot 176. The connection bar 175 has a clamping feature 177 that locks the connection bar 175 to the first element 172 when the clamping feature 177 is actuated. The second element 176 has a feature (not visible) that interlocks with the first element 172 at the bottom to hold the bottom of element 174 in place after the clamping feature 177 is tightened.

Figure 12D:
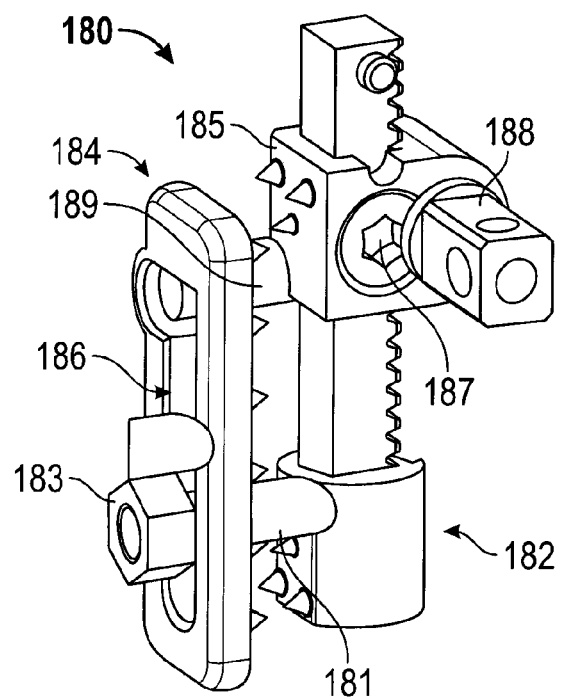
FIG. 12D illustrates an installation tool adapted for use with the devices of FIGS. 12A-12C.

FIG. 12D illustrates a device 180 that is similar to device 170 of FIGS. 12A-12C. The device 180 has a first element 182 and a second element 184 with a slot 186. The first element 182 includes a post 181 that bridges the distance between elements 182, 184 and fit into the slot 186. There is a nut 183 attached to the end of the bridging post 181. The device 180 includes a connection element 185 with a bridging post 189 that fits into a notch that is part of slot 186. The connection element 185 also has a clamping feature 187 that locks the connection element 185 to the first element 182 when the clamping feature 187 is actuated. A tool 188 attaches to the connection element 185 and comprises a toothed wheel (not visible in FIG. 12D) that engages the toothed surface visible on the side of first element 182 and, when activated, distracts the bridging post 189 of the connection element 185 vertically from the bridging post 181 of the first element 182.

Figure 13A:
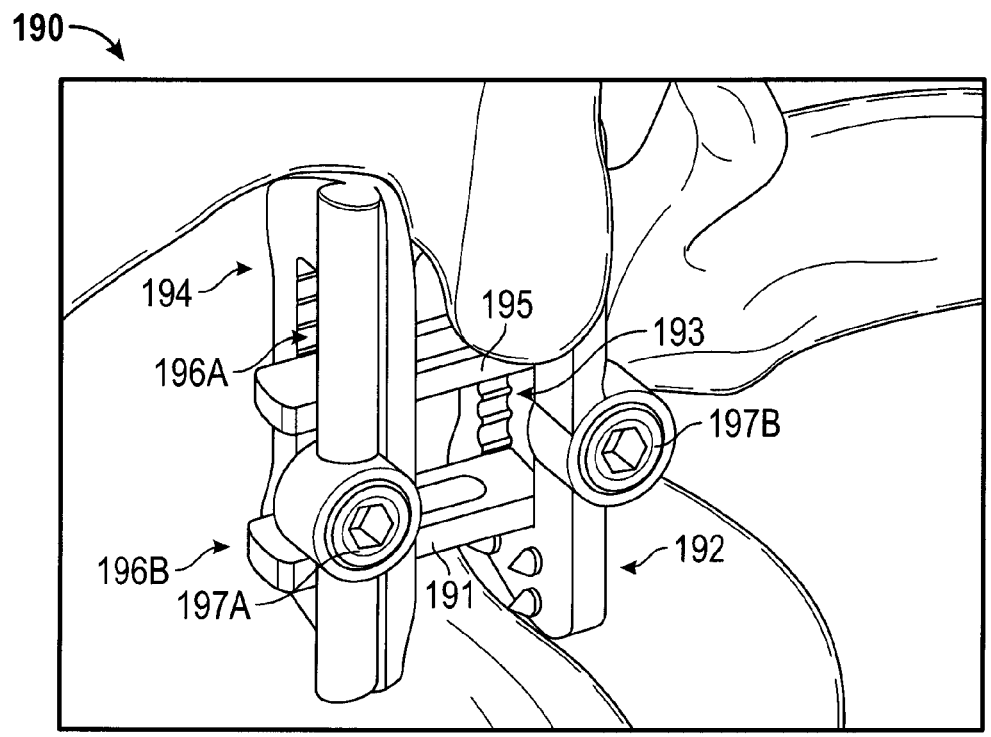
FIGS. 13A-13B are perspective views of another embodiment of a spinous process device according to certain aspects of this disclosure.
Figure 13B:
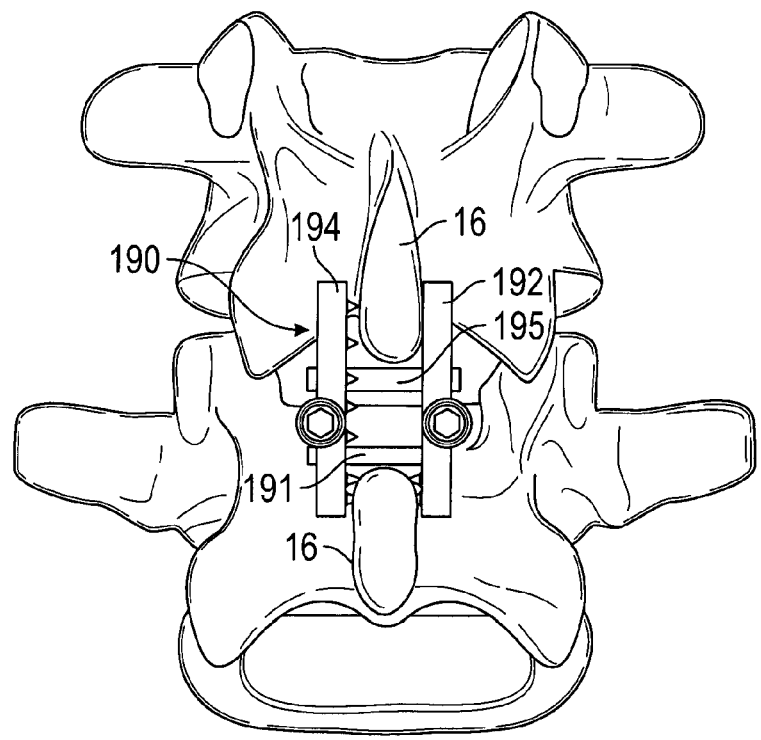

FIGS. 13A-13B are perspective views of another embodiment of a spinous process device 190 according to certain aspects of this disclosure. The device 190 has a first element 192 with a slot 193 and a second element 194 with slots 196A and 196B. The first element 192 includes a bar 191 that bridges the distance between elements 192, 194 and fit into the slot 196B. The device 190 also has a connection bar 195 that also bridges the distance between the elements 192, 194 and fits into the slots 193 and 196A at each end. The first element 192 has a clamping feature 197B that locks one end of connection bar 195 to the slot 193 when the clamping feature 197B is actuated. The second element 194 has a clamping feature 197A that locks the other end of connection bar 195 to the slot 196A and locks the end of bar 191 to slot 196B when the clamping feature 197A is actuated.

Figure 14A:
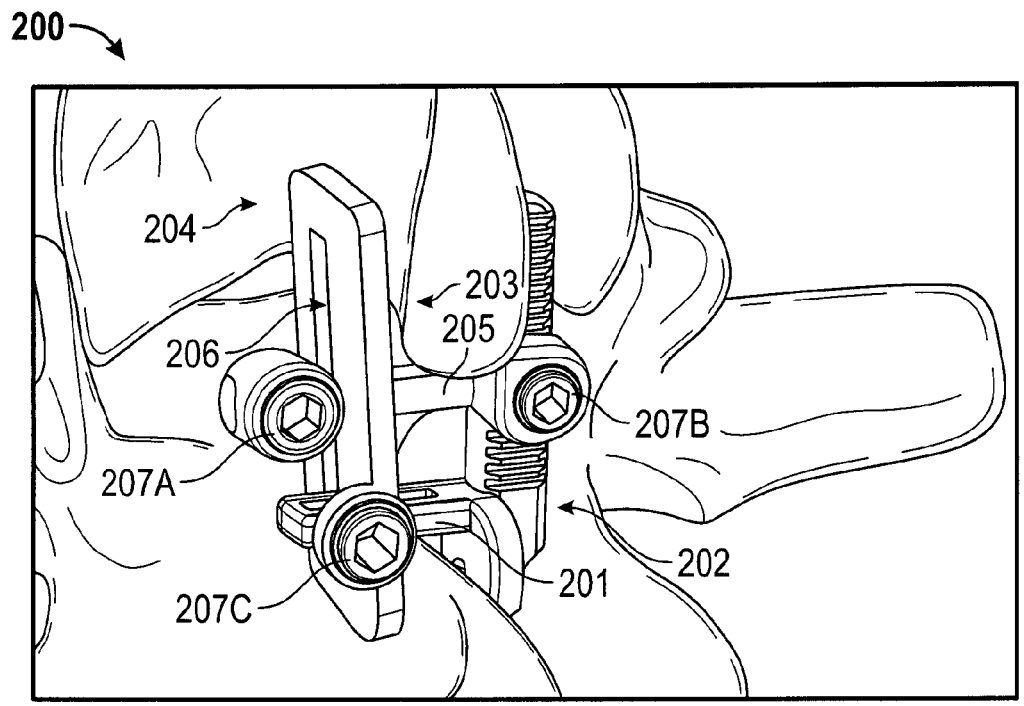
FIGS. 14A-14B are perspective views of another embodiment of a spinous process device according to certain aspects of this disclosure.
Figure 14B:
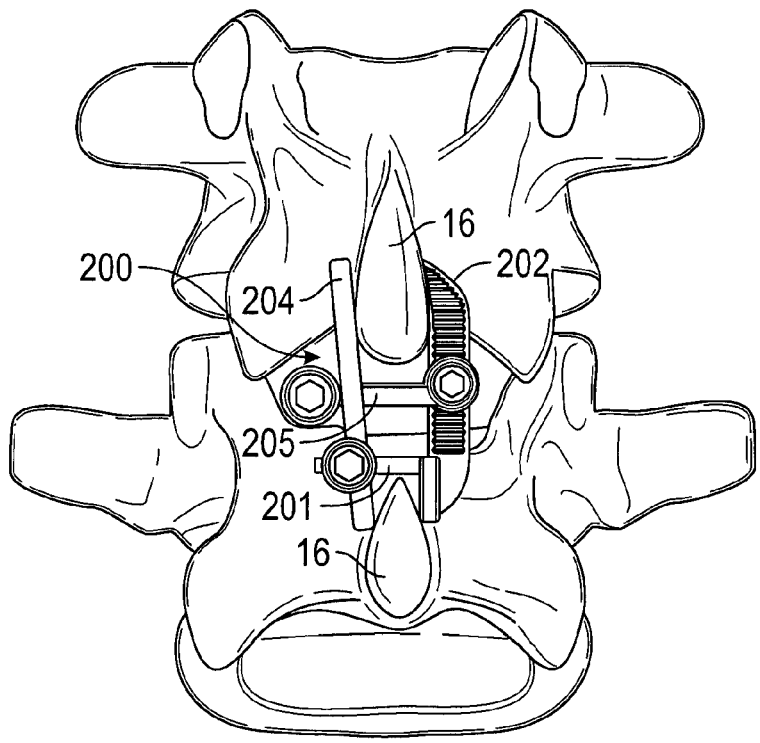

FIGS. 14A-14B are perspective views of another embodiment of a spinous process device 200 according to certain aspects of this disclosure. The device 200 has a first element 202 and a second element 204 with slot 206. The first element 202 includes a bar 201 that bridges the distance between elements 202, 204 and fit into the slot 206. The device 200 also has a connection bar 205 that also bridges the distance between the elements 202, 204 and fits through the slot 206 at one end and includes a clamping feature 207B at the other end that locks that end of connection bar 205 to the first element 202 when the clamping feature 207B is actuated. The device 200 also includes a locking element 207A that locks the other end of the connection bar 205 and prevents the connection bar 205 from being withdrawn from the slot 206. Second element 204 also includes a clamping feature 207C that, when actuated, locks the end of bar 201 to the slot 206.

Figure 15C:
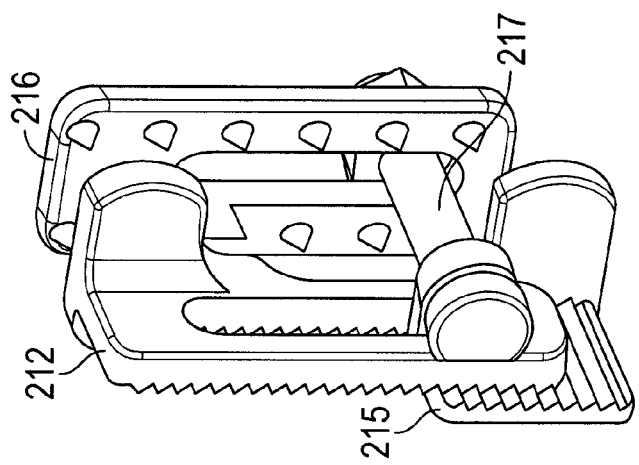
FIGS. 15A-15C are perspective views of another embodiment of a spinous process device according to certain aspects of this disclosure.
Figure 15B:
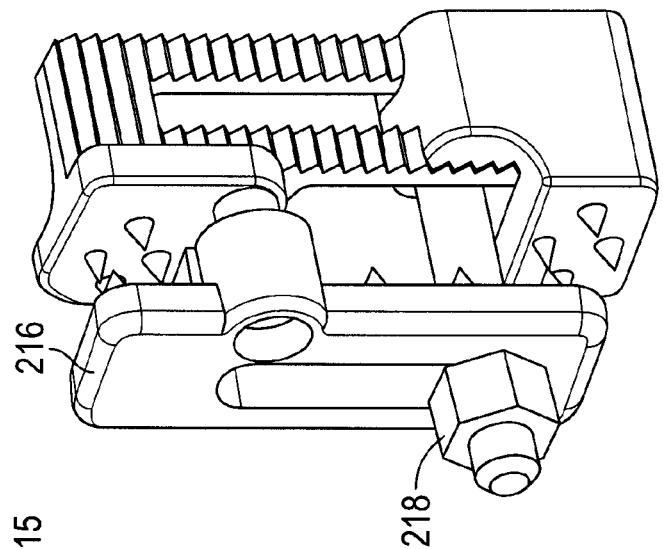
Figure 15A:
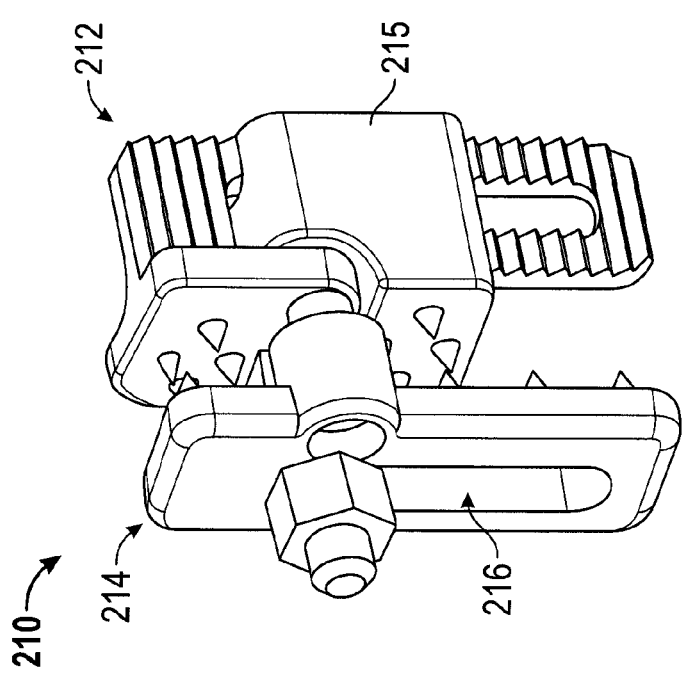

FIGS. 15A-15C are perspective views of another embodiment of a spinous process device 210 according to certain aspects of this disclosure. The device 210 has a first element 212 and a second element 214 with slot 216. The first element 212 includes a post that couples to the second element 214. The device 210 also has a sliding element 215 that is slidably coupled to element 212. The device 210 also has a clamping bolt 217 that passes through the sliding element 215 and through the slot 216. A nut 218 attaches to the end of bolt 217 and, when tightened, clamps the first and second elements 212, 214 to the spinous processes between them.

Figure 16A:
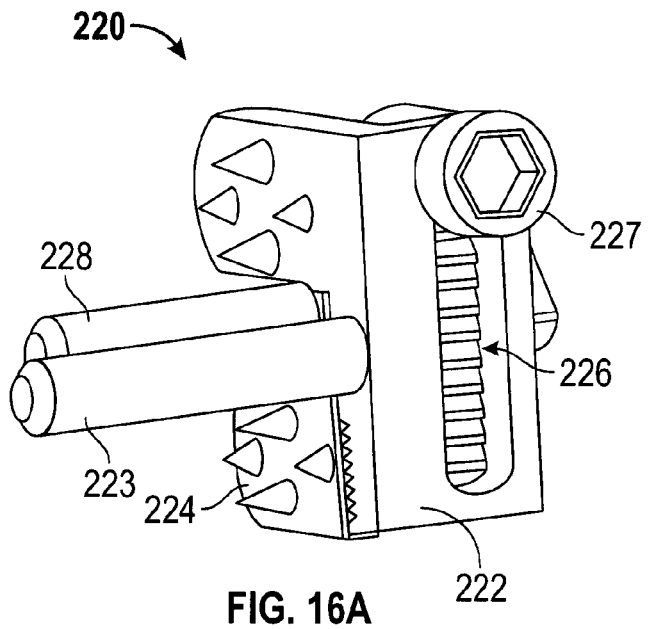
FIGS. 16A-16C are perspective views of another embodiment of a spinous process device according to certain aspects of this disclosure.
Figure 16B:
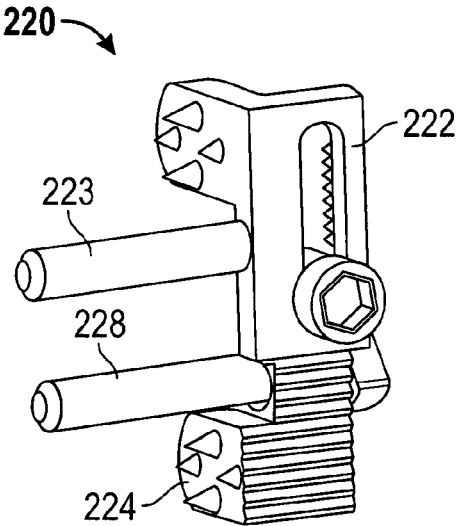
Figure 16C:
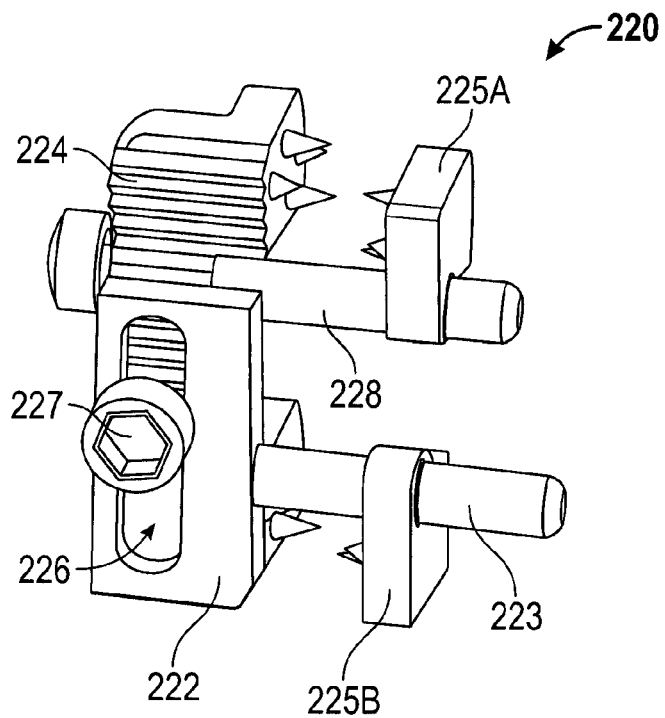

FIGS. 16A-16C are perspective views of another embodiment of a spinous process device 220 according to certain aspects of this disclosure. The device 220 has a first element 222 with slot 226 and a second element 224. The first element 222 includes a post 223 and the second element includes a post 228. The device 220 has a bolt 227 that passes through slot 226 and is threaded into the second element 224 and, when actuated, clamps the first and second elements 222, 224 together. The device 210 also has a pair of plates 225A, 225B that can be slipped over the ends of the posts 228 and 223, respectively, and be clamped to the posts 228 and 223, thereby clamping the spinous processes 16 (not shown in FIGS. 16A-16C) between the plates 225A, 225B and the first and second elements 222, 224.

Figure 17A:
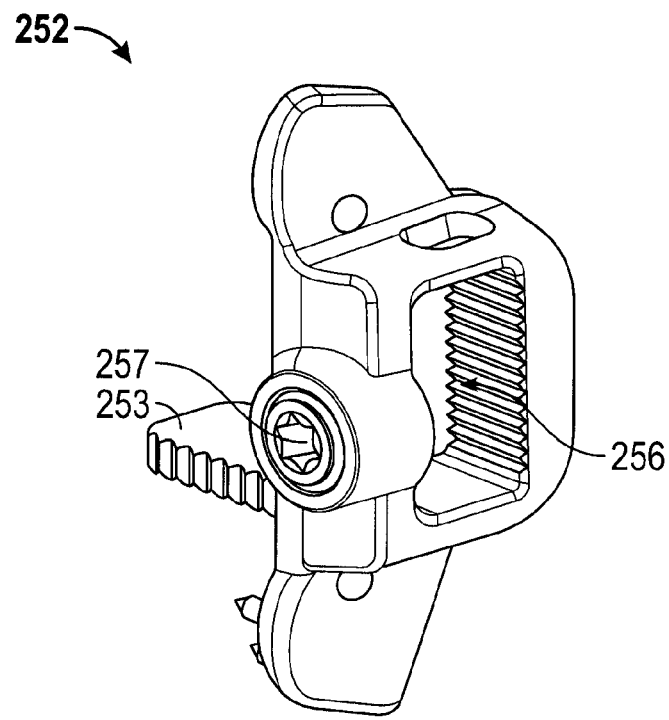
FIGS. 17A-17B are perspective views of another embodiment of a spinous process element according to certain aspects of this disclosure.
Figure 17B:
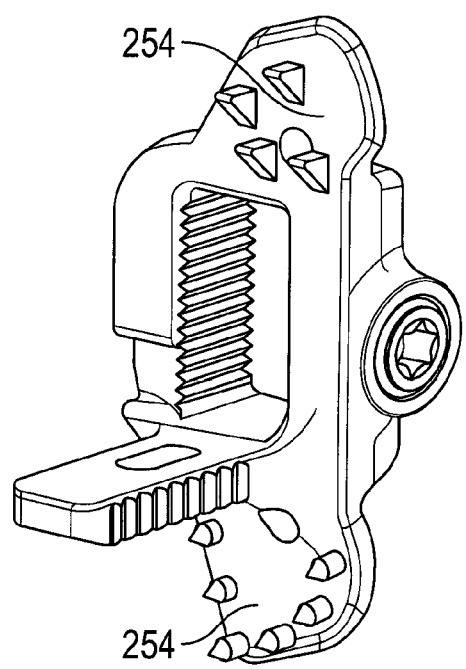
Figure 18A:
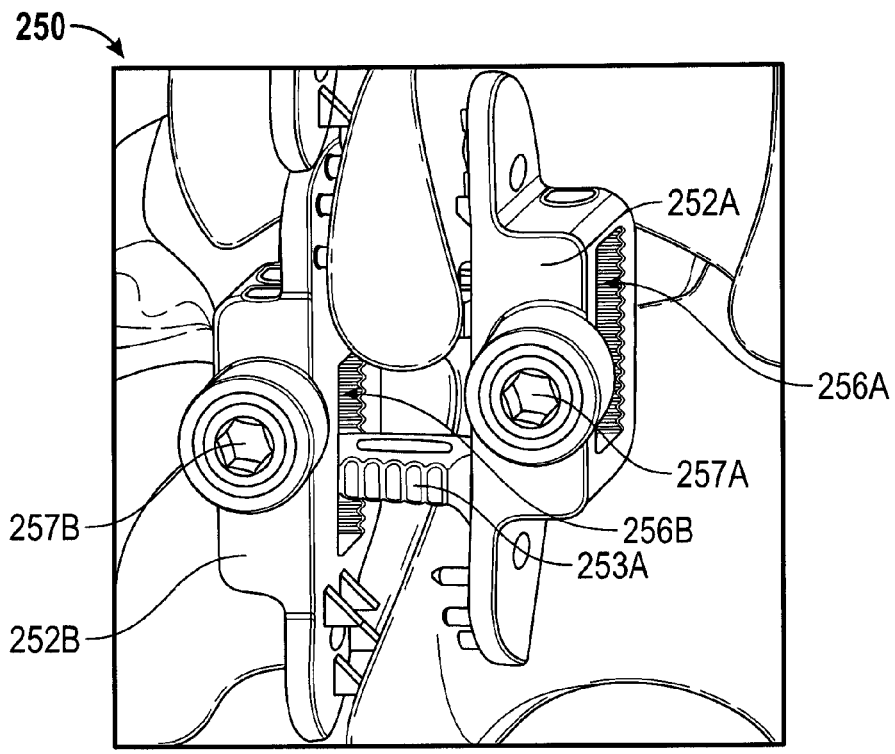
FIGS. 18A-18B are perspective views of the spinous process device formed from two of the elements of FIGS. 17A-17B according to certain aspects of this disclosure.

FIGS. 17A-17B are perspective views of another embodiment of a spinous process element 252 according to certain aspects of this disclosure. A pair of elements 252 are used together as shown in FIG. 18A to form a spinous process device 250. Each element 252 has a gripping plate 254 with upper and lower profiles with gripping features, for example spikes or angled teeth as shown in FIG. 17B, as well as a slot 256. The element 252 also has a connection bar 253 projecting perpendicular to the gripping plate 254. The element 252 also includes a clamping feature 257. The connection bar 253 can be seen to have vertical grooves on the front face, as oriented in FIGS. 17A-17B, and has horizontal grooves (not visible in FIGS. 17A-17B) on the back face. The slot 256 can be seen to have horizontal grooves on the rear interior surface while the front interior surface of slot 156 is smooth. The clamping feature 257 comprises a rear surface (not visible in FIGS. 17A-17B) that protrudes into slot 256 when actuated. The rear surface of clamping feature 257 has vertical grooves that engage vertical grooves on the front face of connection bar 253 of a second spinous process element 252 (not shown in FIGS. 17A-17B) when the clamping feature 257 is tightened.

Figure 18B:
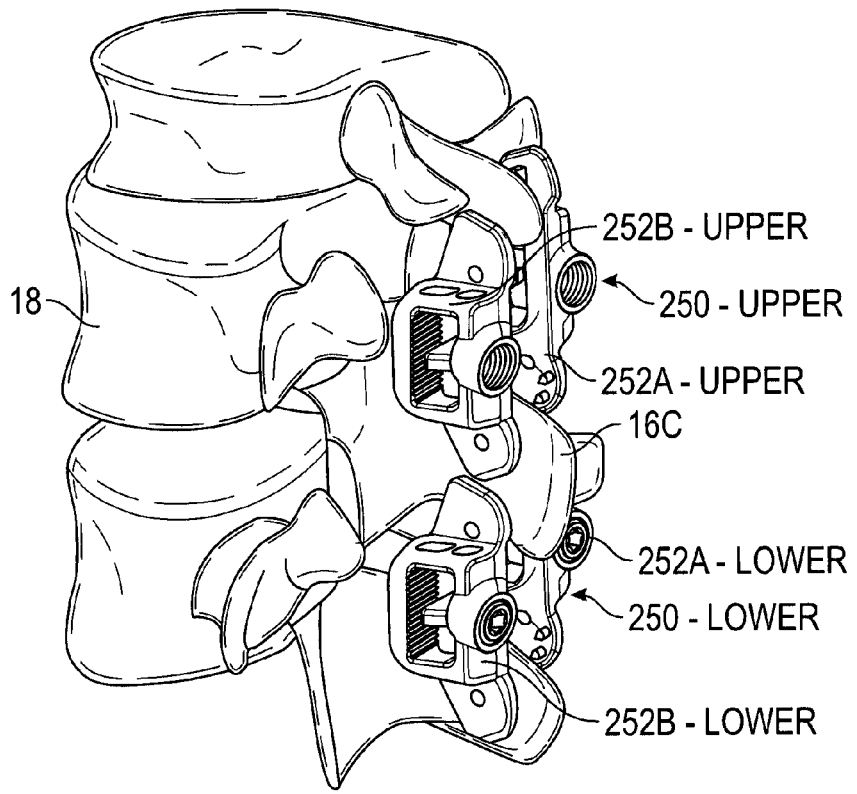

FIGS. 18A-18B are perspective views of the spinous process device 250 formed from two of the spinous process elements 252 of FIGS. 17A-17B according to certain aspects of this disclosure. It can be seen how a first element 252A is positioned on the right side of the spinous processes and a second element 252B is positioned in an inverted orientation on the left side. The connection bar 253A thus fits into the slot 256B where it will be locked by clamping feature 257B when actuated. Similarly, the connection bar 253B fits into slot 256A and will be locked by clamping feature 257A.

FIG. 18B illustrates how multiple devices 250 may be positioned to stabilize adjacent pairs of spinous processes. It can be seen that the upper and lower profiles of the gripping plate 254 are configured such that when element 252B-UPPER of the upper device 250-UPPER is adjacent to element 252B-LOWER of the lower device 250-LOWER, the adjacent profiles cooperate to allow close mounting of the devices 250. Elements 252A and 252B are shaped to allow a pair of spinous process devices 252 to grip a common spinous process 16C so as to stabilize adjacent pairs of spinous processes 16, wherein the elements 252 of the spinous process device 250 each comprise an upper profile and a lower profile such that a top of the first element 252A-LOWER of a lower spinous process device 250-LOWER and a bottom of the first element 252A-UPPER of an upper spinous process device 250-UPPER can be positioned to grip a first side of the common spinous process 16C and a top of the second element 252A-LOWER of the lower spinous process device 250-LOWER and a bottom of the second element 252A-UPPER of the upper spinous process device 250-UPPER can be positioned to grip a second side that is opposite to the first side of the common spinous process 16C.

Figure 19:
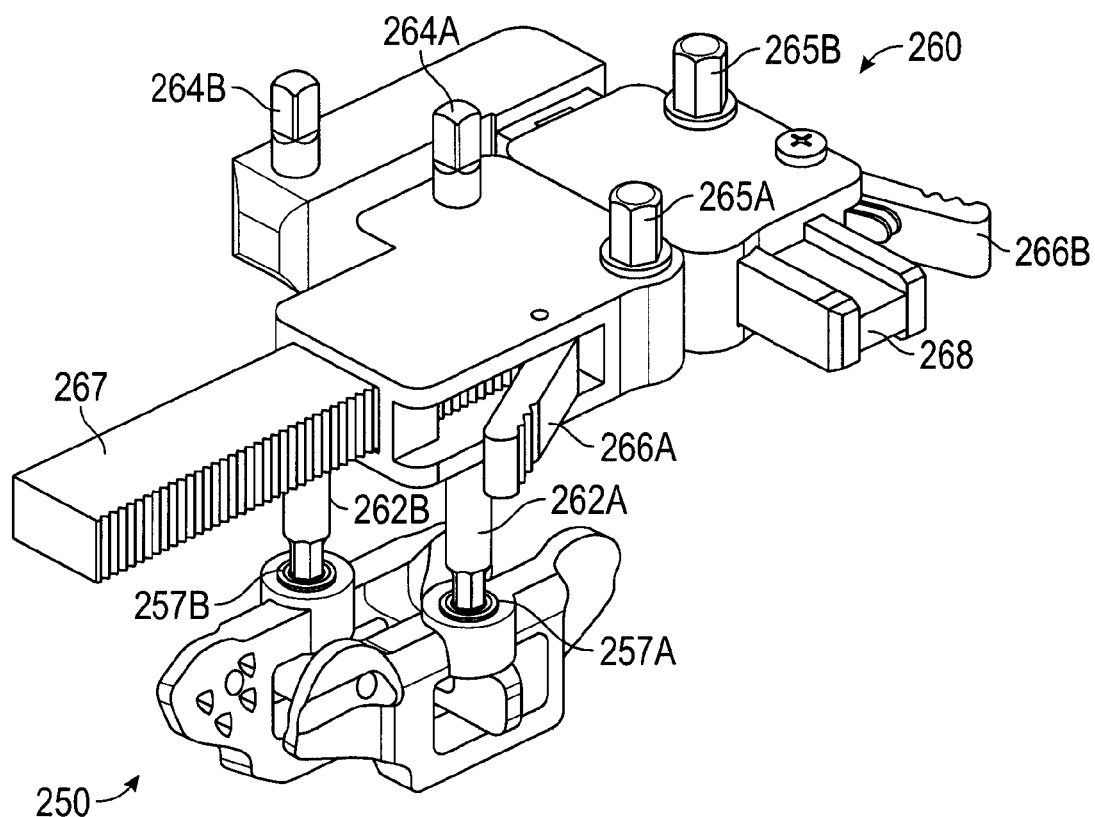
FIG. 19 illustrates an exemplary embodiment of an installation tool adapted for use with the devices of FIGS. 18A-18B according to certain aspects of this disclosure.

FIG. 19 illustrates an exemplary embodiment of an installation tool 260 adapted for use with the device 250 of FIGS. 18A-18B according to certain aspects of this disclosure. The tool 260 has two posts 262A and 262B that engage the clamping features 257A and 257B, respectively, of the device 250. The posts 262A, 262B have drive ends 264A, 264B at the opposite ends that allow the clamping features 257A, 257B to be actuated by use of a tightening tool (not shown), such as a socket wrench for example. The tool 260 includes a first slide 267 with an advancement feature 265A that, when actuated, causes the post 262A to move along a first axis with respect to post 262B. The tool 260 also includes a second slide 268 with advancement feature 265B that, when actuated, causes the post 262A to move with respect to post 262B along a second axis that is perpendicular to the first axis. Ratchets 266A and 266B release the slides 267, 268 respectively when actuated, thereby allowing the tool 260 to be removed.

Figure 20:
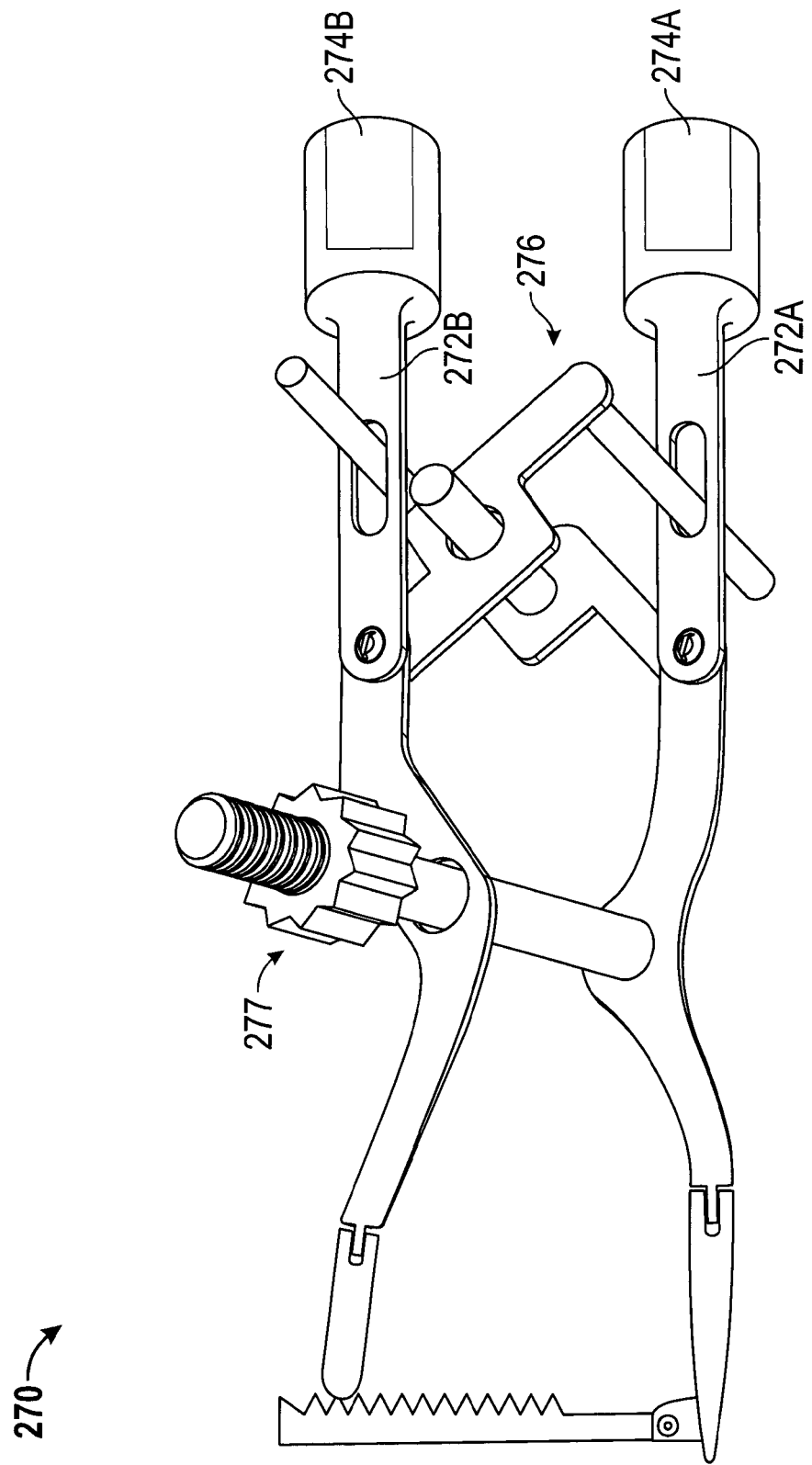
FIG. 20 illustrates another embodiment of an installation tool adapted for use with the device of FIGS. 18A-18B according to certain aspects of this disclosure.

FIG. 20 illustrates another embodiment of an installation tool 270 adapted for use with the device 50 of FIGS. 18A-18B according to certain aspects of this disclosure. The tool 270 includes two handles 272A, 272B that have connection tips 274A, 274B that are configured to engage attachment features (not shown in FIGS. 18A-18B) so as to enable a surgeon to use this tool to position the spinous process elements 252A and 252B. The arms 272A and 272 B are coupled together with a mechanism 276 that maintains the lower portions of the arms 272A, 272B approximately parallel as the separation between the tips 274A, 274B changes. Once separated, the separation of tips 274A and 274B can be maintained by actuation of the rod and nut assembly 277, which can be tightened to hold the upper portions of arms 272A, 272B together or at a designated separation distance.

Figure 21A:
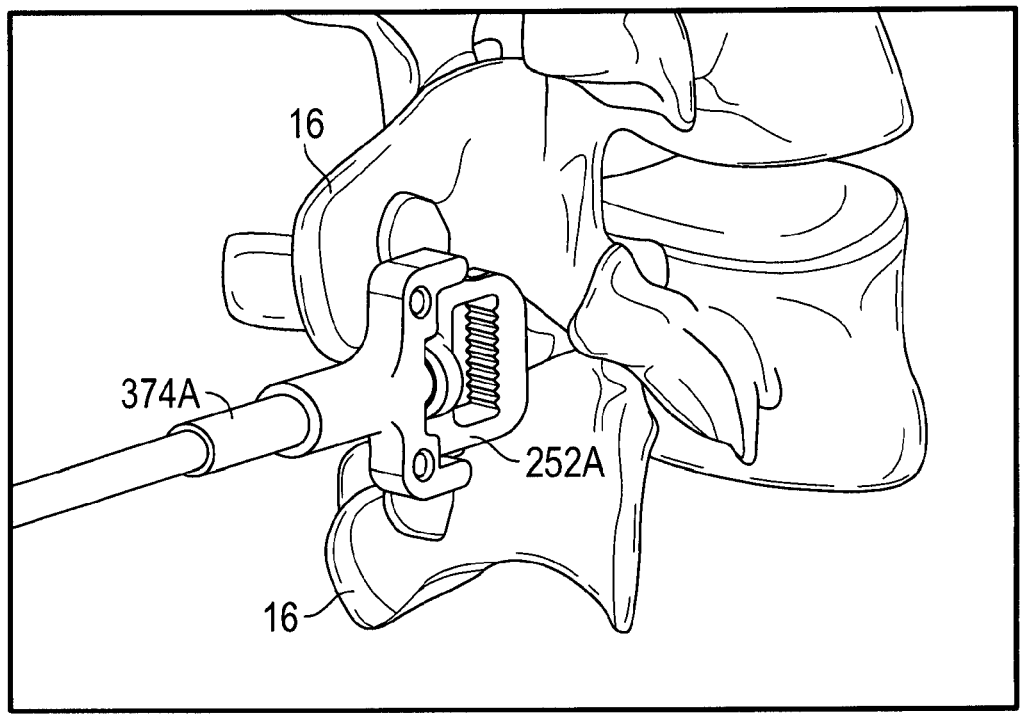
FIGS. 21A-21B illustrate another embodiment of the installation tool of FIG. 20 according to certain aspects of this disclosure.
Figure 21B:
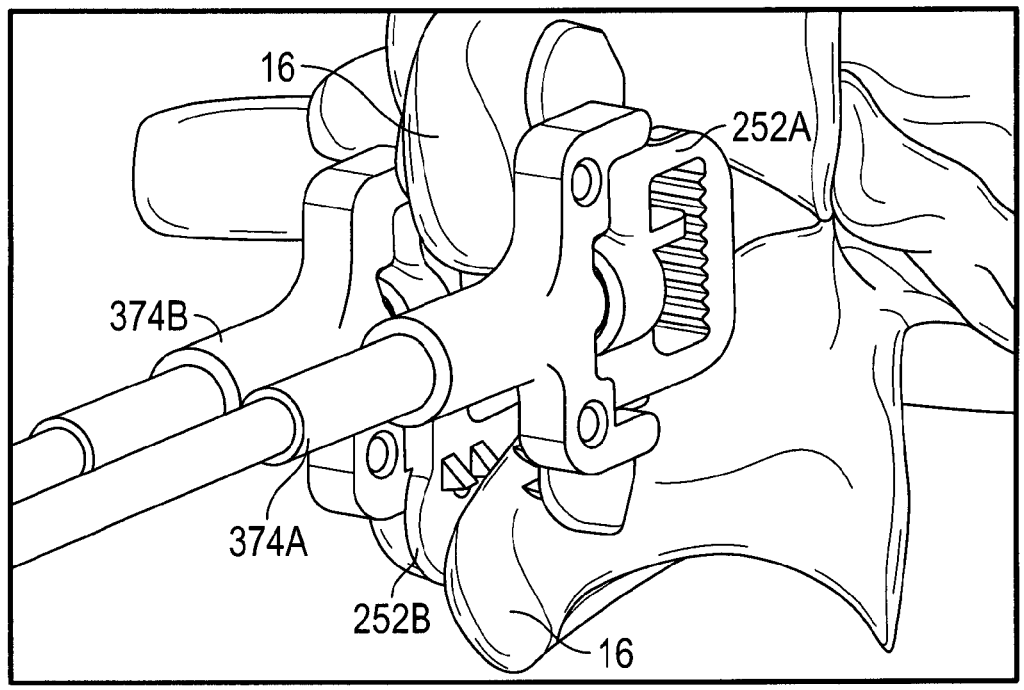

FIGS. 21A-21B illustrate another embodiment of an installation tool 370 according to certain aspects of this disclosure. A first installation tool 370 comprises a tip 374A that engages the clamping feature 257 and also engages the gripping plate 254 of a first spinous process element 252A to allow control of the orientation of the spinous process element 252A. A tip 374B of a second tool 370 engages the clamping feature 257 and gripping plate 254 of a second spinous process element 252B. The tool 370 comprises an internal shaft (not visible in FIGS. 21A-12B) that allows the surgeon to tighten the clamping features 257 of both spinous process elements 252A, 252B while the tool tips 374A, 374B are still engaged.

In some embodiments, a first element, a spacer element, and a second element of a spinous process device can be assembled prior to implantation. The first element, spacer element, and second element can be as disclosed herein, thus a further description of them is not repeated here. In some embodiments, when the device is assembled, the first separation bar and the adjustment bar pass through the locking feature such that the first and second gripping sides or surfaces face each other and the first and second separation bars extend between the first and second gripping sides or surfaces. In some embodiments, the first and second separation bares are generally parallel to each other in an initial assembled state or as adjusted assembled state. The assembled spinous process device can have a first distance between the first and second gripping surfaces and a second distance between the first and second separation bars.

In summary, certain embodiments of the disclosed spinous process device can be assembled prior to implantation between adjacent spinous processes of different sizes and then adjusted after implantation to securely grip both sides of both adjacent spinous processes as well as a provide positive separation of the adjacent spinous processes. Furthermore, the multiple components of certain embodiments of the disclosed spinous process devices can all be fixedly secured by actuation of a single locking feature. Exemplary tools are disclosed for the manipulation of the disclosed spinous process devices during implantation, adjustment of the relative positions and orientations of the components of the disclosed spinous process device, and actuation of the locking feature.

This application includes description to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "upper," "lower," "left," "right," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Although the relationships among various components are described herein and/or are illustrated as being orthogonal or perpendicular, those components can be arranged in other configurations in some embodiments. For example, the angles formed between the referenced components can be greater or less than 90 degrees in some embodiments.

Although various components are illustrated as being flat and/or straight, those components can have other configurations, such as curved or tapered for example, in some embodiments.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such as an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A device for immobilizing adjacent spinous processes, the device comprising:
   a first element comprising a first element side configured to grip first process sides of the adjacent spinous processes and comprising a first separation bar projecting to the first element side in a first direction such that the first separation bar extends between the adjacent spinous processes when the first element side engages the adjacent spinous processes;

a spacer element comprising an adjustment bar and a second separation bar fixedly coupled to and projecting from the adjustment bar such that the adjustment bar and the second separation bar are not collinear; and a second element comprising (a) a second element side configured to grip second process sides of the adjacent spinous processes, (b) a receptacle configured to receive the first separation bar in the first direction, (c) a hole configured to receive the adjustment bar in a second direction, the second direction being transverse to the first direction, and (d) a clamping feature configured to selectably lock the first separation bar and the adjustment bar relative to each other and to the second element, the clamping feature having a locked configuration and an unlocked configuration; and wherein when the first element, the second element, and the spacer element are assembled with the clamping feature in the unlocked configuration, the spacer element is translatable in the second direction relative to the second element; and wherein the second separation bar extends between the adjacent spinous processes when the adjustment bar is in the hole and the second element side engages the adjacent spinous processes.

2. The device of claim 1, wherein:
the second element further comprises a channel extending in a direction that is generally parallel to the second element side; and
the channel is configured (a) to accept the adjustment bar such that the second separation bar is oriented generally perpendicular to the second element side and (b) to allow the spacer element to move in the channel in a direction generally parallel to the second element side.

3. The device of claim 1, wherein:
when the first element, the second element, and the spacer element are assembled with the clamping feature in the unlocked configuration, both (a) a first distance between the first and second element sides is adjustable in the first direction and (b) a second distance between the first and second separation bars is adjustable in the second direction.

4. The device of claim 3, wherein when the clamping feature is in the unlocked configuration, the first distance is continuously adjustable within a first range and the second distance is continuously adjustable within a second range.

5. The device of claim 3, wherein when the first element, the second element, and the spacer element are assembled with the clamping feature in the unlocked configuration, the second distance is adjustable independently of the first distance.

6. The device of claim 1, wherein the second direction is perpendicular to the first direction.

7. The device of claim 1, wherein the adjacent spinous processes are spaced from each other in a superior-inferior direction, and the second direction is the superior-inferior direction.

8. The device of claim 1, wherein:
the first element side has a superior end and an inferior end; and
when the first element, the second element, and the spacer element are assembled with the clamping feature in the unlocked configuration, (i) an inferior side of the first separation bar is closer to the inferior end than is positionable an inferior side of the second separation bar, and (ii) a superior side of the first separation bar is positioned farther from the superior end than is positionable a superior side of the second separation bar.

9. The device of claim 1, wherein an external surface of the first separation bar is configured to contact one of said adjacent spinous processes and an external surface of the second separation bar is configured to contact another of said adjacent spinous processes.

10. The device of claim 1, wherein when the first element, the second element, and the spacer element are assembled with the clamping feature in the unlocked configuration, the adjustment bar is slidable in the second direction, relative to the clamping feature, at the second element.

11. The device of claim 1, wherein a longest dimension of the second separation bar extends perpendicular to a longest dimension of the adjustment bar.

12. The device of claim 1, wherein, in a cross-section perpendicular to a longest dimension of the first separation bar and through the first separation bar and the second separation bar when the first element, the second element, and the spacer element are assembled, the first separation bar has a centroid located outside of the perimeter of the second separation bar, and the second separation bar has a centroid that is located outside the perimeter of the first separation bar.

13. The device of claim 1, wherein, when the first element, the second element, and the spacer element are assembled and the first and second element sides engage the adjacent spinous processes, all of the first separation bar is positioned superior or inferior relative to all of the second separation bar.

14. A system comprising the device of claim 1 and an insertion tool, the insertion tool comprising:
a first arm configured to engage one of the first and second elements of the device;
a second arm coupled to the first arm, the second arm configured to engage the other of the first and second elements of the device, the first and second arms configured to hold the first and second elements at an angle to each other within an angular range and to selectably adjust an average distance between the first and second elements; and
a third arm coupled to one of the first and second arms, the third arm configured to selectably separate the first and second separation bars.

15. A device for immobilizing adjacent spinous processes, the adjacent spinous processes being spaced from each other in a superior-inferior direction, the device comprising:
a first element configured to grip a first side of said adjacent spinous processes and comprising a first separation bar configured to extend between said spinous processes when the first element grips said adjacent spinous processes;
a second element configured to grip a second opposed side of said adjacent spinous processes, and comprising (a) a receptacle configured to receive the first separation bar, (b) a hole extending through the second element in a superior-inferior direction, and (b) a locking feature having an unlocked configuration and a locked configuration; and
a spacer element comprising an adjustment bar and a second separation bar fixedly coupled to and projecting from the adjustment bar, the second separation bar configured to extend between said adjacent spinous processes when the second element grips said adjacent spinous processes and the adjustment bar is positioned in the hole; and wherein when the first element, the second element, and the spacer element are assembled with the first separation bar received by the second element, the adjustment bar positioned in the hole, and said locking feature in the unlocked configuration, (a) relative motion between said first element and said second element is permitted and (b) relative translation of said first separation bar and said second separation bar is permitted in the superior-inferior direction, and wherein when the first separation bar is received by the second element, the adjustment bar is positioned in the hole, and said locking feature is in the locked configuration, said first element and said second element are fixed relative to each other and said first and second separation bars are fixed relative to each other.

16. The device of claim 15, wherein when said locking feature is in the unlocked configuration, said relative motion between said first element and said second element comprises one or both of (a) a change in a first distance between said first element and said second element or (b) a change in a first relative angle between said first element and said second element.

17. The device of claim 15, wherein when said locking feature is in the unlocked configuration, said relative motion between said first separation bar and said second separation bar comprises one or both of (a) a change in a second distance between said first separation bar and said second separation bar or (b) a change in a second relative angle between said first separation bar and said second separation bar.

18. The device of claim 15, wherein:
the locking feature comprises a first axis;
the first separation bar comprises a second axis that is generally aligned with a longest dimension of the first separation bar;
when the first element, the second element, and the spacer element are assembled with the locking feature in the unlocked configuration, the locking feature allows the first separation bar to move along the second axis and rotate about the first axis; and
when the first element, the second element, and the spacer element are assembled with the locking feature in the locked configuration, the locking feature locks the first separation bar at a position and an angle relative to the locking feature.

19. The device of claim 15, wherein when the first element, the second element, and the spacer element are assembled with the locking feature in the unlocked configuration, the first element is allowed to rotate with respect to the second element.

20. The device of claim 15, wherein said locking feature is configured to lock said first separation bar and said second separation bar in any of a plurality of orientations relative to each other.

21. The device of claim 15, wherein said locking feature is configured to lock said first element and said second element in any of a plurality of orientations relative to each other.

22. The device of claim 15, wherein when said locking feature is in the unlocked configuration, said spacer element is loosely captured within said second element.

23. An assembly comprising two of the devices of claim 15, wherein a first of said two devices is an upper device and a second of said two devices is a lower device, wherein the first elements and the second elements of the two devices are shaped to allow both the upper device and the lower device to grip a common spinous process, wherein the first and second elements of the upper device each comprise a lower profile and the first and second elements of the lower device each comprise an upper profile, the lower profiles and the upper profiles being configured such that (a) a top of the first element of the lower device and a bottom of the first element of the upper device can be positioned to grip a first side of the common spinous process and (b) a top of the second element of the lower device and a bottom of the second element of the upper device can be positioned to grip a second side that is opposite to the first side of the common spinous process.

24. A method of stabilizing adjacent vertebrae having spinous processes, the method comprising the steps of:
implanting the device of claim 1 into a patient such that the first and second elements are disposed on opposite sides of the adjacent spinous processes and the first and second separation bars are disposed between the adjacent spinous processes.

25. The method of claim 24, wherein (i) when the first element, the second element, and the spacer element are assembled, the device has a first distance between the first and second elements, and a second distance between the first and second separation bars, and (ii) the method further comprises the steps of:
adjusting the second distance so as to bring the first and second separation bars into contact with the adjacent spinous processes;
adjusting the first distance and an angle between the first and second element sides so as to bring the first and second element sides into contact with the adjacent spinous processes; and
activating the clamping feature to lock the first separation bar and the adjustment bar.

26. The method of claim 25, wherein said first separation bar and said second separation bar are nonparallel to each other when said first separation bar and said adjustment bar are locked.

27. The method of claim 25, wherein said first element and said second element are nonparallel to each other when said first separation bar and said adjustment bar are locked.

28. The method of claim 24, wherein:
the method further comprises the step of connecting an insertion tool to the device, wherein the insertion tool comprises a first arm configured to engage one of the first and second elements, a second arm coupled to the first arm and configured to engage the other of the first and second elements wherein the first and second arms are configured to hold the first and second elements at an angle to each other within an angular range and to selectably adjust a first distance between the first and second element sides, and a third arm coupled to one of the first and second arms, the third arm configured to selectably separate the first and second separation bars; and
the step of implanting comprises adjusting, after positioning the device in the patient, the first distance using the first and second arms such that the first and second element sides contact the opposite sides of the adjacent spinous processes and adjusting a second distance between the first and second separation bars using the third arm such that the first and second separation bars contact the adjacent spinous processes.

29. A system comprising:
a device for immobilizing adjacent spinous processes, the device comprising:
a first element comprising a first element side configured to grip first process sides of the adjacent spinous processes and comprising a first separation bar projecting to the first element side;
a spacer element comprising an adjustment bar and a second separation bar projecting from the adjustment bar such that the adjustment bar and the second separation bar are not collinear; and a second element comprising a second element side configured to grip second process sides of the adjacent spinous processes and comprising a clamping feature configured to selectably lock the first separation bar and the adjustment bar; and an insertion tool comprising:

a first arm configured to engage one of the first and second elements of the device;

a second arm coupled to the first arm, the second arm configured to engage the other of the first and second elements of the device, the first and second arms configured to hold the first and second elements at an angle to each other within an angular range and to selectably adjust an average distance between the first and second elements; and a third arm coupled to one of the first and second arms, the third arm configured to selectably separate the first and second separation bars.

* * * * *